(12) United States Patent
Shirazi

(10) Patent No.: US 8,796,186 B2
(45) Date of Patent: Aug. 5, 2014

(54) SYSTEM AND METHOD FOR PROCESSING LARGE NUMBER OF BIOLOGICAL MICROARRAYS

(75) Inventor: Mohsen Shirazi, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 530 days.

(21) Appl. No.: 12/481,852

(22) Filed: Jun. 10, 2009

(65) Prior Publication Data

US 2010/0069265 A1 Mar. 18, 2010

Related U.S. Application Data

(63) Continuation of application No. 11/389,549, filed on Mar. 24, 2006, now abandoned.

(60) Provisional application No. 60/669,130, filed on Apr. 6, 2005.

(51) Int. Cl.
*C40B 60/12* (2006.01)
*C12M 1/36* (2006.01)
*G01N 21/00* (2006.01)

(52) U.S. Cl.
USPC .... 506/39; 435/283.1; 435/286.2; 435/287.2; 422/63; 422/82.05

(58) Field of Classification Search
None
See application file for complete search history.

(56) References Cited

U.S. PATENT DOCUMENTS

| | | | |
|---|---|---|---|
| 2,371,061 A | 3/1945 | Milano | |
| 2,610,419 A | 9/1952 | Baumbach | |
| 3,281,860 A | 10/1966 | Adams et al. | |
| 3,690,836 A | 9/1972 | Buissiere et al. | |
| 3,710,933 A | 1/1973 | Fulwyler et al. | |
| 3,802,966 A | 4/1974 | Delekto et al. | |
| 4,016,855 A | 4/1977 | Mimata | |
| 4,121,222 A | 10/1978 | Diebold et al. | |
| 4,200,110 A | 4/1980 | Peterson et al. | |
| 4,204,929 A | 5/1980 | Bier | |
| 4,325,910 A | 4/1982 | Jordan | |
| 4,349,510 A | 9/1982 | Kolehmainen et al. | |

(Continued)

FOREIGN PATENT DOCUMENTS

| CA | 2305545 | 4/1999 |
|---|---|---|
| CA | 2335951 | 12/1999 |

(Continued)

OTHER PUBLICATIONS

Dynal Inc., Biomagnetic Techniques in Molecular Biology, A Technical Handbook 3rd Edition pp. 7-10, 48-50, (1998).

(Continued)

*Primary Examiner* — Betty Forman
(74) *Attorney, Agent, or Firm* — Alston and Bird LLP

(57) ABSTRACT

A system and method for processing biological sensors. The system includes a support component configured to support a fluidic component. The fluidic component includes at least a first container and a second container. The first container is capable of holding a first volume of a first fluid, and the second container is capable of holding a second volume of a second fluid. Additionally, the system includes a hybridization component configured to perform a hybridization process on a first sensor and a second sensor. Moreover, the system includes a transport component configured to move the first sensor, directly or indirectly, from the hybridization component into the first container and in contact with the first volume of the first fluid.

27 Claims, 24 Drawing Sheets

(56) References Cited

U.S. PATENT DOCUMENTS

| | | |
|---|---|---|
| 4,373,071 A | 2/1983 | Itakura |
| 4,458,066 A | 7/1984 | Caruthers et al. |
| 4,499,052 A | 2/1985 | Fulwyler |
| 4,500,707 A | 2/1985 | Caruthers et al. |
| 4,665,034 A | 5/1987 | Chandler |
| 4,672,040 A | 6/1987 | Josephson |
| 4,682,895 A | 7/1987 | Costello |
| 4,707,454 A | 11/1987 | Hendrix |
| 4,728,502 A | 3/1988 | Hamill |
| 4,731,325 A | 3/1988 | Palva et al. |
| 4,731,335 A | 3/1988 | Brigati |
| 4,764,671 A | 8/1988 | Park |
| 4,780,504 A | 10/1988 | Buendia et al. |
| 4,785,814 A | 11/1988 | Kane |
| 4,812,512 A | 3/1989 | Buendia et al. |
| 4,815,274 A | 3/1989 | Piatti |
| 4,822,746 A | 4/1989 | Walt |
| 4,824,789 A | 4/1989 | Yafuso et al. |
| 4,829,010 A | 5/1989 | Chang |
| 4,853,335 A | 8/1989 | Olsen et al. |
| 4,859,419 A | 8/1989 | Marks et al. |
| 4,877,745 A | 10/1989 | Hayes et al. |
| 4,878,971 A | 11/1989 | Tsunekawa et al. |
| 4,879,097 A | 11/1989 | Whitehead et al. |
| 4,889,611 A | 12/1989 | Blough, Jr. |
| 4,895,706 A | 1/1990 | Root et al. |
| 4,922,092 A | 5/1990 | Rushbrooke et al. |
| 4,963,498 A | 10/1990 | Hillman et al. |
| 4,988,617 A | 1/1991 | Landegren et al. |
| 4,992,383 A | 2/1991 | Farnsworth |
| 4,999,306 A | 3/1991 | Yafuso et al. |
| 5,002,867 A | 3/1991 | Macevicz |
| 5,021,550 A | 6/1991 | Zeiger |
| 5,028,545 A | 7/1991 | Soini |
| 5,047,524 A | 9/1991 | Andrus et al. |
| 5,073,029 A | 12/1991 | Eberly et al. |
| 5,075,077 A | 12/1991 | Durley et al. |
| 5,087,820 A | 2/1992 | Kearns et al. |
| 5,100,775 A | 3/1992 | Smyczek et al. |
| 5,104,792 A | 4/1992 | Silver et al. |
| 5,104,808 A | 4/1992 | Laska et al. |
| 5,105,305 A | 4/1992 | Betzig et al. |
| 5,114,864 A | 5/1992 | Walt |
| 5,126,276 A | 6/1992 | Fish et al. |
| 5,132,242 A | 7/1992 | Cheung |
| 5,133,374 A | 7/1992 | Druding et al. |
| 5,141,813 A | 8/1992 | Nelson |
| 5,143,853 A | 9/1992 | Walt |
| 5,143,854 A | 9/1992 | Pirrung et al. |
| 5,144,136 A | 9/1992 | Kubisiak |
| 5,153,319 A | 10/1992 | Caruthers et al. |
| 5,154,888 A | 10/1992 | Zander et al. |
| 5,170,659 A | 12/1992 | Kemp |
| 5,176,881 A | 1/1993 | Sepaniak et al. |
| 5,184,634 A | 2/1993 | Kitajima |
| 5,188,963 A | 2/1993 | Stapleton |
| 5,194,300 A | 3/1993 | Cheung |
| 5,200,051 A | 4/1993 | Cozzette et al. |
| 5,204,253 A | 4/1993 | Sanford et al. |
| 5,215,131 A | 6/1993 | Poy |
| 5,219,712 A | 6/1993 | Evans et al. |
| 5,229,297 A | 7/1993 | Schniplesky et al. |
| 5,230,866 A | 7/1993 | Shartle et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt et al. |
| 5,254,477 A | 10/1993 | Walt et al. |
| 5,256,549 A | 10/1993 | Urdea et al. |
| 5,258,781 A | 11/1993 | John |
| 5,278,048 A | 1/1994 | Parce et al. |
| 5,279,721 A | 1/1994 | Schmid |
| 5,281,516 A | 1/1994 | Stapleton et al. |
| 5,281,540 A | 1/1994 | Merkh et al. |
| 5,287,272 A | 2/1994 | Rutenberg et al. |
| 5,288,463 A | 2/1994 | Chemelli |
| 5,288,514 A | 2/1994 | Ellman |
| 5,296,195 A | 3/1994 | Pang et al. |
| 5,298,741 A | 3/1994 | Walt et al. |
| 5,300,779 A | 4/1994 | Hillman et al. |
| 5,302,509 A | 4/1994 | Cheeseman |
| 5,304,487 A | 4/1994 | Wilding et al. |
| 5,310,469 A | 5/1994 | Cunningham et al. |
| 5,314,829 A | 5/1994 | Coles |
| 5,320,808 A | 6/1994 | Holen et al. |
| 5,320,814 A | 6/1994 | Walt et al. |
| 5,322,799 A | 6/1994 | Miller et al. |
| 5,324,633 A | 6/1994 | Fodor et al. |
| 5,346,672 A | 9/1994 | Stapleton et al. |
| 5,352,609 A | 10/1994 | Boquet |
| 5,357,590 A | 10/1994 | Auracher |
| 5,358,691 A | 10/1994 | Clark et al. |
| 5,374,395 A | 12/1994 | Robinson et al. |
| 5,380,489 A | 1/1995 | Sutton et al. |
| 5,382,511 A | 1/1995 | Stapleton |
| 5,384,261 A | 1/1995 | Winkler et al. |
| 5,395,587 A | 3/1995 | Brigham-Burke et al. |
| 5,422,271 A | 6/1995 | Chen et al. |
| 5,424,186 A | 6/1995 | Fodor et al. |
| 5,435,724 A | 7/1995 | Goodman et al. |
| 5,436,129 A | 7/1995 | Stapleton et al. |
| 5,443,791 A | 8/1995 | Cathcart et al. |
| 5,445,970 A | 8/1995 | Rohr et al. |
| 5,447,837 A | 9/1995 | Urnovitz et al. |
| 5,451,500 A | 9/1995 | Stapleton et al. |
| 5,481,629 A | 1/1996 | Tabuchi et al. |
| 5,486,335 A | 1/1996 | Wilding et al. |
| 5,489,678 A | 2/1996 | Fodor et al. |
| 5,494,798 A | 2/1996 | Gerdt et al. |
| 5,496,997 A | 3/1996 | Pope |
| 5,500,187 A | 3/1996 | Deoms et al. |
| 5,512,490 A | 4/1996 | Walt et al. |
| 5,516,635 A | 5/1996 | Ekins et al. |
| 5,518,883 A | 5/1996 | Soini |
| 5,527,673 A | 6/1996 | Reinhartz et al. |
| 5,543,329 A | 8/1996 | Bedell |
| 5,545,531 A | 8/1996 | Rava et al. |
| 5,549,974 A | 8/1996 | Holmes |
| 5,565,324 A | 10/1996 | Still et al. |
| 5,573,909 A | 11/1996 | Singer et al. |
| 5,575,849 A | 11/1996 | Honda et al. |
| 5,578,832 A | 11/1996 | Trulson et al. |
| 5,587,128 A | 12/1996 | Wilding et al. |
| 5,591,384 A | 1/1997 | Abrams et al. |
| 5,593,838 A | 1/1997 | Zanzucchi et al. |
| 5,593,839 A | 1/1997 | Hubbell et al. |
| 5,595,908 A | 1/1997 | Fawcett et al. |
| 5,595,915 A | 1/1997 | Geysen |
| 5,599,504 A | 2/1997 | Hosoi et al. |
| 5,601,650 A | 2/1997 | Goldbecker |
| 5,618,671 A | 4/1997 | Lindstrom |
| 5,618,701 A | 4/1997 | Landegren |
| 5,627,041 A | 5/1997 | Shartle et al. |
| 5,628,849 A | 5/1997 | Fasano et al. |
| 5,633,972 A | 5/1997 | Walt et al. |
| 5,635,358 A | 6/1997 | Wilding et al. |
| 5,637,469 A | 6/1997 | Wilding et al. |
| 5,639,603 A | 6/1997 | Dower et al. |
| 5,649,576 A | 7/1997 | Kirk et al. |
| 5,652,149 A | 7/1997 | Mileaf et al. |
| 5,656,241 A | 8/1997 | Seifert et al. |
| 5,658,802 A | 8/1997 | Hayes et al. |
| 5,674,698 A | 10/1997 | Zarling et al. |
| 5,674,743 A | 10/1997 | Ulmer |
| 5,675,700 A | 10/1997 | Atwood et al. |
| 5,682,232 A | 10/1997 | Tajima et al. |
| 5,683,916 A | 11/1997 | Goffe et al. |
| 5,690,894 A | 11/1997 | Pinkel et al. |
| 5,698,450 A | 12/1997 | Ringrose et al. |
| 5,716,825 A | 2/1998 | Hancock et al. |
| 5,726,010 A | 3/1998 | Clark |
| 5,726,013 A | 3/1998 | Clark |
| 5,759,784 A | 6/1998 | Asp et al. |
| 5,770,157 A | 6/1998 | Cargill et al. |

(56) References Cited

U.S. PATENT DOCUMENTS

| | | |
|---|---|---|
| 5,784,152 A | 7/1998 | Heffelfinger et al. |
| 5,800,992 A | 9/1998 | Fodor et al. |
| 5,804,384 A | 9/1998 | Muller et al. |
| 5,807,522 A | 9/1998 | Brown et al. |
| 5,812,511 A | 9/1998 | Kawamura et al. |
| 5,814,524 A | 9/1998 | Walt et al. |
| 5,834,758 A | 11/1998 | Trulson et al. |
| 5,837,196 A | 11/1998 | Pinkel et al. |
| 5,837,860 A | 11/1998 | Anderson et al. |
| 5,840,256 A | 11/1998 | Demers et al. |
| 5,843,767 A | 12/1998 | Beattie |
| 5,854,684 A | 12/1998 | Stabile et al. |
| 5,863,708 A | 1/1999 | Zanzucchi et al. |
| 5,863,722 A | 1/1999 | Brenner |
| 5,866,434 A | 2/1999 | Massey et al. |
| 5,869,004 A | 2/1999 | Parce et al. |
| 5,874,219 A | 2/1999 | Rava et al. |
| 5,876,946 A | 3/1999 | Burbaum et al. |
| 5,888,723 A | 3/1999 | Sutton et al. |
| 5,888,834 A | 3/1999 | Ishikawa et al. |
| 5,900,481 A | 5/1999 | Lough et al. |
| 5,922,617 A | 7/1999 | Wang et al. |
| 5,945,334 A | 8/1999 | Besemer et al. |
| 5,981,180 A | 11/1999 | Chandler et al. |
| 6,023,540 A | 2/2000 | Walt et al. |
| 6,025,601 A | 2/2000 | Trulson et al. |
| 6,037,186 A | 3/2000 | Stimpson |
| 6,040,138 A | 3/2000 | Lockhart et al. |
| 6,050,278 A | 4/2000 | Arnal et al. |
| 6,060,022 A | 5/2000 | Pang et al. |
| 6,071,748 A | 6/2000 | Modlin et al. |
| 6,074,614 A | 6/2000 | Hafeman et al. |
| 6,083,763 A | 7/2000 | Balch |
| 6,090,553 A | 7/2000 | Matson |
| 6,100,084 A | 8/2000 | Miles et al. |
| 6,114,122 A | 9/2000 | Besemer et al. |
| 6,132,685 A | 10/2000 | Kercso et al. |
| 6,143,496 A | 11/2000 | Brown et al. |
| 6,165,778 A | 12/2000 | Kedar |
| 6,170,494 B1 | 1/2001 | Marinaro et al. |
| 6,191,852 B1 | 2/2001 | Paffhausen et al. |
| 6,210,910 B1 | 4/2001 | Walt et al. |
| 6,232,066 B1 | 5/2001 | Felder et al. |
| 6,235,479 B1 | 5/2001 | Rogers |
| 6,268,131 B1 | 7/2001 | Kang et al. |
| 6,269,846 B1 | 8/2001 | Overbeck et al. |
| 6,271,145 B1 | 8/2001 | Toda |
| 6,308,721 B1 | 10/2001 | Bock et al. |
| 6,326,211 B1 | 12/2001 | Anderson et al. |
| 6,327,410 B1 | 12/2001 | Walt et al. |
| 6,340,588 B1 | 1/2002 | Nova et al. |
| 6,355,431 B1 | 3/2002 | Chee et al. |
| 6,361,940 B1 | 3/2002 | Van Ness et al. |
| 6,391,623 B1 | 5/2002 | Besemer et al. |
| 6,396,995 B1 | 5/2002 | Stuelpnagel et al. |
| 6,406,845 B1 | 6/2002 | Walt et al. |
| 6,422,249 B1 | 7/2002 | Certa et al. |
| 6,429,027 B1 | 8/2002 | Chee et al. |
| 6,432,696 B2 | 8/2002 | Custance et al. |
| 6,458,323 B1 | 10/2002 | Boekstegers |
| 6,458,533 B1 | 10/2002 | Felder et al. |
| 6,519,032 B1 | 2/2003 | Kuebler et al. |
| 6,544,732 B1 | 4/2003 | Chee et al. |
| 6,551,817 B2 | 4/2003 | Besemer et al. |
| 6,594,006 B1 * | 7/2003 | Muehlhoff et al. ...... 356/139.03 |
| 6,604,902 B2 | 8/2003 | Norris et al. |
| 6,613,513 B1 | 9/2003 | Parce et al. |
| 6,620,584 B1 | 9/2003 | Chee et al. |
| 6,646,272 B2 | 11/2003 | Rushbrooke et al. |
| 6,660,233 B1 | 12/2003 | Coassin et al. |
| 6,663,832 B2 | 12/2003 | Lebl et al. |
| 6,716,629 B2 | 4/2004 | Hess et al. |
| 6,770,441 B2 | 8/2004 | Dickinson et al. |
| 6,830,936 B2 | 12/2004 | Anderson et al. |
| 6,858,394 B1 | 2/2005 | Chee et al. |
| 6,890,741 B2 | 5/2005 | Fan et al. |
| 6,905,816 B2 | 6/2005 | Jacobs et al. |
| 6,991,939 B2 | 1/2006 | Walt et al. |
| 6,998,274 B2 | 2/2006 | Chee et al. |
| 7,033,761 B2 | 4/2006 | Shafer |
| 7,043,939 B2 | 5/2006 | Imahashi |
| 7,060,431 B2 | 6/2006 | Chee et al. |
| 7,115,884 B1 | 10/2006 | Walt et al. |
| 7,129,554 B2 | 10/2006 | Lieber et al. |
| 7,142,290 B2 | 11/2006 | Tsien et al. |
| 7,332,127 B2 | 2/2008 | Kim et al. |
| 7,462,469 B2 * | 12/2008 | Bass et al. ...................... 435/91.2 |
| 7,476,360 B2 | 1/2009 | Gau et al. |
| 7,510,841 B2 | 3/2009 | Stuelpnagel et al. |
| 7,612,020 B2 | 11/2009 | Stuelpnagel et al. |
| 7,641,871 B2 | 1/2010 | Futami et al. |
| 7,901,897 B2 | 3/2011 | Stuelpnagel et al. |
| 2002/0055167 A1 | 5/2002 | Pourahmadi et al. |
| 2002/0119077 A1 * | 8/2002 | Shumate et al. .............. 422/100 |
| 2002/0150909 A1 | 10/2002 | Stuelpnagel et al. |
| 2002/0164653 A1 * | 11/2002 | Downs ........................... 435/7.1 |
| 2002/0177141 A1 | 11/2002 | Chee et al. |
| 2003/0032204 A1 | 2/2003 | Walt et al. |
| 2003/0044991 A1 * | 3/2003 | Haslam et al. .................. 436/47 |
| 2003/0059930 A1 | 3/2003 | Gazeau |
| 2003/0096239 A1 | 5/2003 | Gunderson et al. |
| 2003/0108867 A1 | 6/2003 | Chee et al. |
| 2003/0108900 A1 | 6/2003 | Oliphant et al. |
| 2003/0148362 A1 | 8/2003 | Luka |
| 2003/0162210 A1 | 8/2003 | Chetverin et al. |
| 2003/0162304 A1 | 8/2003 | Dority et al. |
| 2004/0120861 A1 | 6/2004 | Petroff |
| 2004/0191807 A1 * | 9/2004 | Shirazi et al. ..................... 435/6 |
| 2005/0158702 A1 | 7/2005 | Stuelpnagel et al. |
| 2006/0034913 A1 | 2/2006 | Gaede et al. |
| 2006/0234371 A1 | 10/2006 | Shirazi |
| 2006/0246576 A1 | 11/2006 | Shirazi |
| 2007/0099288 A1 | 5/2007 | Gao et al. |
| 2007/0267335 A1 | 11/2007 | Gao et al. |
| 2007/0267782 A1 | 11/2007 | Gao et al. |
| 2008/0003667 A1 | 1/2008 | Jones et al. |
| 2008/0038712 A1 | 2/2008 | Gao et al. |
| 2008/0038714 A1 | 2/2008 | Gao et al. |
| 2008/0311585 A1 | 12/2008 | Gao et al. |
| 2009/0215649 A1 | 8/2009 | Stuelpnagel et al. |
| 2009/0227472 A1 | 9/2009 | Stuelpnagel et al. |
| 2010/0081583 A1 * | 4/2010 | Shirazi ............................ 506/33 |
| 2011/0009297 A1 | 1/2011 | Jones et al. |

FOREIGN PATENT DOCUMENTS

| | | |
|---|---|---|
| EP | 0234612 | 9/1987 |
| EP | 0260965 | 3/1988 |
| EP | 0269764 | 6/1988 |
| EP | 0378968 | 7/1990 |
| EP | 0392546 | 10/1990 |
| EP | 0417305 | 3/1991 |
| EP | 0478319 | 4/1992 |
| EP | 0723146 | 7/1996 |
| EP | 01141712 | 10/2001 |
| GB | 2315131 | 1/1998 |
| GB | 2349349 | 11/2000 |
| WO | WO 89/11101 | 11/1986 |
| WO | WO 89/10977 | 11/1989 |
| WO | WO 89/11548 | 11/1989 |
| WO | WO 90/00626 | 1/1990 |
| WO | WO 90/03382 | 4/1990 |
| WO | WO 90/15070 | 12/1990 |
| WO | WO 91/06659 | 5/1991 |
| WO | WO 92/10092 | 6/1992 |
| WO | WO 92/10587 | 6/1992 |
| WO | WO 92/10588 | 6/1992 |
| WO | WO 93/02360 | 2/1993 |
| WO | WO 93/06121 | 4/1993 |
| WO | WO 93/09668 | 5/1993 |
| WO | WO 93/11262 | 6/1993 |
| WO | WO 93/17126 | 9/1993 |
| WO | WO 93/22053 | 11/1993 |
| WO | WO 93/22058 | 11/1993 |

(56) References Cited

FOREIGN PATENT DOCUMENTS

| | | | |
|---|---|---|---|
| WO | WO 94/11388 | 5/1994 | |
| WO | WO 95/20164 | 7/1995 | |
| WO | WO 95/33846 | 12/1995 | |
| WO | WO 96/03212 | 2/1996 | |
| WO | WO 97/14028 | 4/1997 | |
| WO | WO 97/14928 | 4/1997 | |
| WO | WO 97/26539 | 7/1997 | |
| WO | WO 97/27326 | 7/1997 | |
| WO | WO 97/33737 | 9/1997 | |
| WO | WO 97/40385 | 10/1997 | |
| WO | WO 98/08092 | 2/1998 | |
| WO | WO 98/20019 | 5/1998 | |
| WO | WO 98/29736 | 7/1998 | |
| WO | WO 98/40726 | 9/1998 | |
| WO | WO 98/50782 | 11/1998 | |
| WO | WO 98/53093 | 11/1998 | |
| WO | WO 98/53300 | 11/1998 | |
| WO | WO 99/05320 | 2/1999 | |
| WO | WO 99/18434 | 4/1999 | |
| WO | WO 99/60170 | 11/1999 | |
| WO | WO 99/67414 | 12/1999 | |
| WO | WO 99/67641 | 12/1999 | |
| WO | WO 00/04372 | 1/2000 | |
| WO | WO 00/13004 | 3/2000 | |
| WO | WO 00/16101 | 3/2000 | |
| WO | WO 00/29619 | * | 5/2000 |
| WO | WO 00/39587 | 7/2000 | |
| WO | WO 00/47996 | 8/2000 | |
| WO | WO 00/48000 | 8/2000 | |
| WO | WO 00/71992 | 11/2000 | |
| WO | WO 01/59432 | 8/2001 | |
| WO | WO 02/00336 | 1/2002 | |
| WO | WO 02/30562 | 4/2002 | |

OTHER PUBLICATIONS

Fodor et al., "Light-Directed, Spatially Addressable Parallel Chemical Synthesis," Science, vol. 251, pp. 767-773 (1991).
Kenis et al., "Microfabrication Inside Capillaries Using Multiphase Laminar Flow Patterning," Science, vol. 285, pp. 83-85 (1999).
Kenis et al., "Fabrication inside Microchannels Using Fluid Flow," Accounts of Chemical Research, 33: 841-847 (2000).
Kononen et al., "Tissue microarrays for high-throughput molecular profiling of tumor specimens," Nat. Med., vol. 4, No. 7, pp. 844-847 (1998).
Nyborg, "Acoustic Streaming," Physical Acoustics, Principles and Methods, vol. II, Part B, chapter 11, pp. 265-331, Edited by W. Mason, Academic Press (1965).
Oosterbroek, Preface in Lab-on-a-Chip, miniaturized systems for (bio) chemical analysis and synthesis. Elsevier, 2003. pp. v-vi.
Sjolander et al., "Integrated Fluid Handling System for Biomolecular Interaction Analysis," Analytical Chemistry, vol. 63, No. 20, pp. 2338-2345 (1991).
Chee et al., "Accessing genetic information with high-density DNA arrays," Science, 274(5287): 610-614 (1996).
Cronin, Section 5.4, "Panel Discussion," in "Pharmacogenetics: Bridging the Gap Between Basic Science and Clinical Application," Transcript of International Business Communications Conference of May 20-22, 1996, Arlington, Virginia (Nov. 1996).
Decision T384/08 of the EPO Technical Board of Appeal (Jun. 26, 2009).
Fodor et al., "Light-directed, spatially addressable parallel chemical synthesis," Science, 251(4995): 767-773 (1991).
Geysen et al., "Strategies for epitope analysis using peptide synthesis," Journal of Immunological Methods, 102: 259-274 (1987).
Helphrey, Section 5.2, "Automation of Oligonucleotide Array Analysis," in "Pharmacogenetics: Bridging the Gap Between Basic Science and Clinical Application," Transcript of International Business Communications Conference of May 20-22, 1996, Arlington, Virginia (Nov. 1996).
Kallioniemi et al., "Tissue microarray technology for high-throughput molecular profiling of cancer," Human Molecular Genetics, 10(7): 657-662 (2001).
Kwiatkowski et al., "A high-capacity manifold support for the detection of specific IgE antibodies in allergic individuals," Journal of Immunological Methods, 168: 137-143 (1994).
Lockhart et al., "Expression monitoring by hybridization to high-density oligonucleotide arrays," Nature Biotechnology, 14(13): 1675-1680 (1996).
Shafer and Hawkins, "DNA variation and the future of human genetics," Nature Biotechnology, 16: 33-39 (1998).
Wang et al., "Large-Scale Identification, Mapping, and Genotyping of Single-Nucleotide Polymorphisms in the Human Genome," Science, 280(5366): 1077-1082 (1998).

* cited by examiner

SYSTEM AND METHOD FOR PROCESSING LARGE NUMBER OF BIOLOGICAL MICROARRAYS

CROSS-REFERENCES TO RELATED APPLICATIONS

This application is a continuation of U.S. patent application Ser. No. 11/389,549, filed on Mar. 24, 2006, which claims priority from U.S. Patent Application No. 60/669,130, filed on Apr. 6, 2005 Each of these applications is incorporated herein in its entirety by reference for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention relates in general to biological microarray techniques. More particularly, the invention provides a system and method for processing a large number of biological microarrays. Merely by way of example, the invention is described as it applies to 96-peg instrumentation, but it should be recognized that the invention has a broader range of applicability.

A biological microarray often includes nucleic acid probes that are used to extract sequence information from nucleic acid samples. The nucleic acid samples are exposed to the nucleic acid probes under certain conditions that would allow hybridization. Afterwards, the biological microarray is processed and scanned to determine to which probes the nucleic acid samples have hybridized. Based on such determination, the sequence information is obtained by comparing patterns of hybridization and non-hybridization. As an example, the sequence information can be used for sequencing nucleic acids, or diagnostic screening for genetic diseases or for the presence of a particular pathogen or a strain of pathogen.

The processing of the biological microarray prior to scanning is often performed by a fluidic system. For example, the fluidic system includes a fluidic station, which can wash and stain the microarray. With the advancement of the microarray design, the fluidic system often needs to be modified in order to improve automation and lower cost.

Hence it is highly desirable to improve techniques for processing microarrays.

BRIEF SUMMARY OF THE INVENTION

The present invention relates in general to biological microarray techniques. More particularly, the invention provides a system and method for processing a large number of biological microarrays. Merely by way of example, the invention is described as it applies to 96-peg instrumentation, but it should be recognized that the invention has a broader range of applicability.

According to one embodiment of the present invention, a system for processing biological sensors includes a support component configured to support a fluidic component. The fluidic component includes at least a first container and a second container. The first container is capable of holding a first volume of a first fluid, and the second container is capable of holding a second volume of a second fluid. Additionally, the system includes a hybridization component configured to perform a hybridization process on a first sensor and a second sensor. Moreover, the system includes a transport component configured to move the first sensor, directly or indirectly, from the hybridization component into the first container and in contact with the first volume of the first fluid. Also, the transport component is further configured to move the second sensor, directly or indirectly, from the hybridization component into the second container and in contact with the second volume of the second fluid. The transport component is further configured to move the first sensor and the second sensor substantially simultaneously.

According to another embodiment of the present invention, a system for processing biological sensors includes a support component configured to support a fluidic component. The fluidic component includes at least a first container and a second container. The first container is capable of holding a first volume of a first fluid, and the second container is capable of holding a second volume of a second fluid. Additionally, the system includes a hybridization component configured to perform a hybridization process on a first sensor and a second sensor based on at least information associated with a predetermined temperature. Moreover, the system includes a transport component including a gripper and at least one motor. The support component includes a drawer for supporting at least the first container and the second container, and the first container and the second container are substantially stationary with respect to the drawer. The gripper is capable of gripping the first sensor and the second sensor substantially simultaneously and of releasing the first sensor and the second sensor substantially simultaneously. The at least one motor is configured to move the gripped first sensor into the first container and in contact with the first volume of the first fluid, move the gripped second sensor into the second container and in contact with the second volume of the second fluid, and move the first sensor and the second sensor substantially simultaneously.

According to yet another embodiment of the present invention, a method for processing biological sensors includes transferring a first sensor and a second sensor into a system for processing biological sensors. The system includes at least a transport component, a hybridization component, and a fluidic component. The transport component includes a gripper, and the fluidic component includes a first container and a second container. The first container holds a first volume of a first fluid, and the second container holds a second volume of a second fluid. Additionally, the method includes after the transferring a first sensor and a second sensor, performing a hybridization process on at least the first sensor and the second sensor by the hybridization component. Moreover, the method includes after the hybridization process, moving the first sensor from the hybridization component, directly or indirectly, into the first container and in contact with the first volume of the first fluid. Also, the method includes after the hybridization process, moving the second sensor from the hybridization component, directly or indirectly, into the second container and in contact with the second volume of the second fluid. The moving the first sensor and the moving the second sensor are performed by at least the gripper, and the moving the first sensor and the moving the second sensor are performed substantially simultaneously.

Many benefits are achieved by way of the present invention over conventional techniques. Certain embodiments of the present invention provide an automated fluidic and hybridization system. For example, the system includes a hybridization oven assembly and provides automatic transportation between the hybridization oven assembly and other components of the system. In another example, the system provides automated transportation to and from a scanner system. Some embodiments of the present invention provide a system that can perform integrated and automated processes for hybridization, wash, and stain. Additionally, coupled with a scanner system, the system can also perform an integrated and automated scanning process. Certain embodiments of the present invention can improve throughput of the hybridization and fluidic system. For example, a plurality of biological sensors, such as microarrays, is processed in parallel. Some embodiments of the present invention can reduce size of the hybridization and fluidic system as well as the scanner system. Certain embodiments of the present invention can reduce cross-contamination between different processes performed on one or more biological sensors. For example, at a given process, different sensors are washed, stained, and/or held in different wells. In another example, a given sensor is washed, stained, and/or held in different wells for different processes respectively. In yet another example, each well is used for at most a single process for at most a single sensor, such as a microarray.

Depending upon embodiment, one or more of these benefits may be achieved. These benefits and various additional objects, features and advantages of the present invention can be fully appreciated with reference to the detailed description and accompanying drawings that follow.

DETAILED DESCRIPTION OF THE INVENTION

Figure 1:
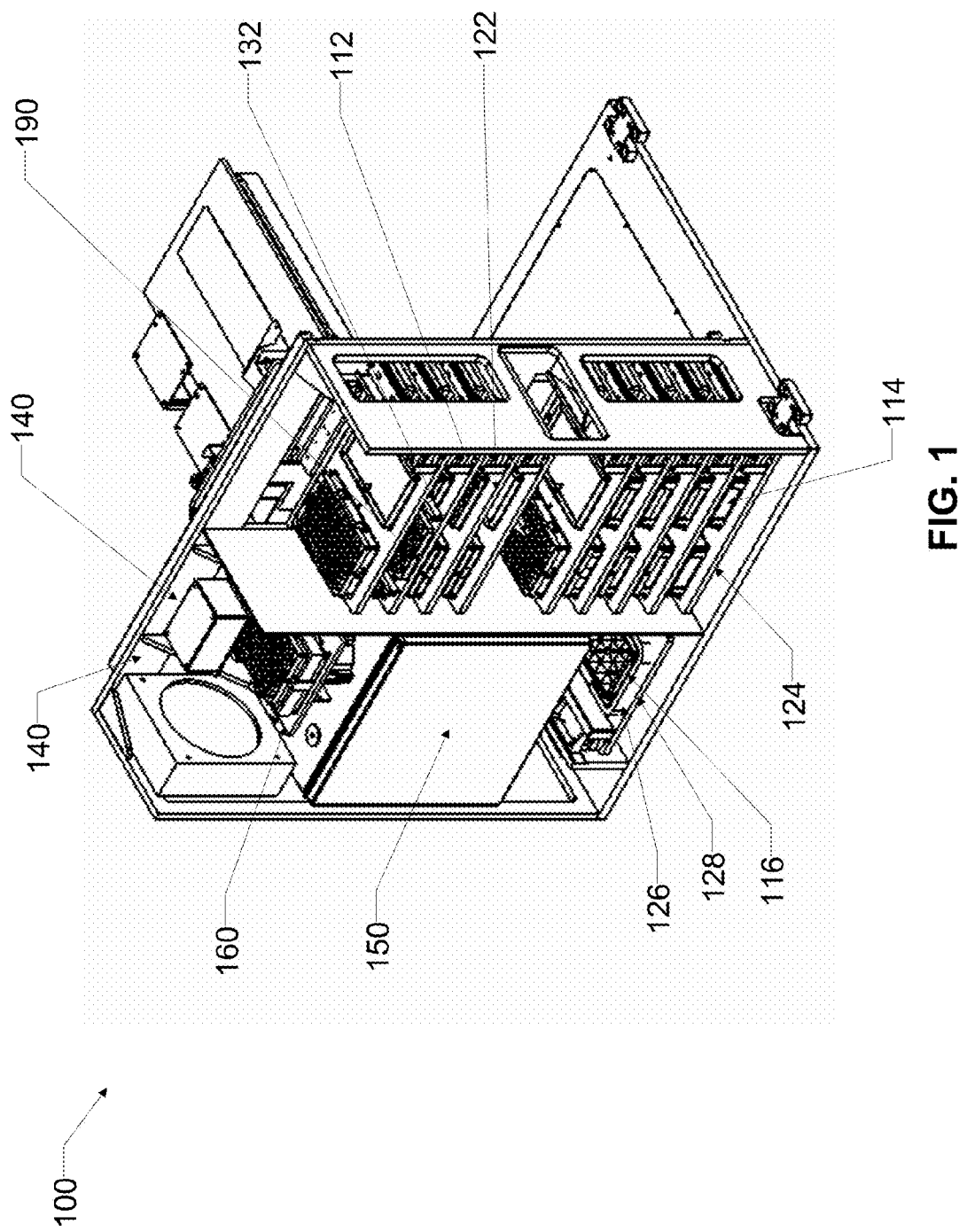
FIGS. 1-2 show a simplified system for processing biological sensors according to an embodiment of the present invention.

The present invention relates in general to biological microarray techniques. More particularly, the invention provides a system and method for processing a large number of biological microarrays. Merely by way of example, the invention is described as it applies to 96-peg instrumentation, but it should be recognized that the invention has a broader range of applicability.

I. General Description

The present invention cites certain patents, applications and other references. When a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252, 743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285 (International Publication Number WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098.

Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 15 10/442,021, 10/013,598 (U.S. Patent Application Publication 20030036069), and U.S. Pat. Nos. 5,856, 092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, NY, 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965, 188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci.* USA 86, 1173 (1989) and WO88/10315), self-sustained sequence replication (Guatelli et al., *Proc. Nat. Acad. Sci.* USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in U.S. Pat. Nos. 5,242, 794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. Patent Application Publication 20030096235), Ser. No. 09/910,292 (U.S. Patent Application Publication 20030082543), and Ser. No. 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davism, *P.N.A.S.* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639;

6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (U.S. Publication No. 20020183936), Ser. Nos. 10/065,856, 10/065,868, 10/328,818, 10/328,872, 10/423,403, and 60/482,389.

II. Definitions

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

Nucleic acid library or array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Biopolymer or biological polymer: is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above. "Biopolymer synthesis" is intended to encompass the synthetic production, both organic and inorganic, of a biopolymer.

Related to a bioploymer is a "biomonomer" which is intended to mean a single unit of biopolymer, or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers. initiation Biomonomer: or "initiator biomonomer" is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

Complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa *Nucleic Acids Res.* 12:203 (1984), incorporated herein by reference.

Combinatorial Synthesis Strategy: A combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

Effective amount refers to an amount sufficient to induce a desired result.

Genome is all the genetic material in the chromosomes of an organism. DNA derived from the genetic material in the chromosomes of a particular organism is genomic DNA.

A genomic library is a collection of clones made from a set of randomly generated overlapping DNA fragments representing the entire genome of an organism. Hybridization conditions will typically include salt concentrations of less than about 1M, more usually less than about 500 mM and preferably less than about 200 mM. Hybridization temperatures can be as low as 5.degree. C., but are typically greater than 22.degree. C., more typically greater than about 30.degree. C., and preferably in excess of about 37.degree. C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Hybridizations, e.g., allele-specific probe hybridizations, are generally performed under stringent conditions. For example, conditions where the salt concentration is no more than about 1 Molar (M) and a temperature of at least 25 degrees Celsius (° C.), e.g., 750 mM NaCl, 50 mM NaPhosphate, 5 mM EDTA, pH 7.4 (5×SSPE) and a temperature of from about 25 to about 30° C.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "*Molecular Cloning A laboratory Manual*" 2nd Ed. Cold Spring Harbor Press (1989) which is hereby incorporated by reference in its entirety for all purposes above.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

Hybridization probes are oligonucleotides capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics.

Hybridizing specifically to: refers to the binding, duplexing, or hybridizing of a molecule only to a particular nucleotide sequence or sequences under stringent conditions when that sequence is present in a complex mixture (e.g., total cellular) DNA or RNA.

Isolated nucleic acid is an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

Ligand: A ligand is a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

Mixed population or complex population: refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

Monomer: refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer.

The term "monomer" also refers to a chemical subunit that can be combined with a different chemical subunit to form a compound larger than either subunit alone. mRNA or mRNA transcripts: as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

Nucleic acid library or array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Nucleic acids according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

Probe: A probe is a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Primer is a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

Receptor: A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

Target: A molecule that has an affinity for a given probe. Targets may be naturally occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

III. Specific Embodiments

Figure 2:
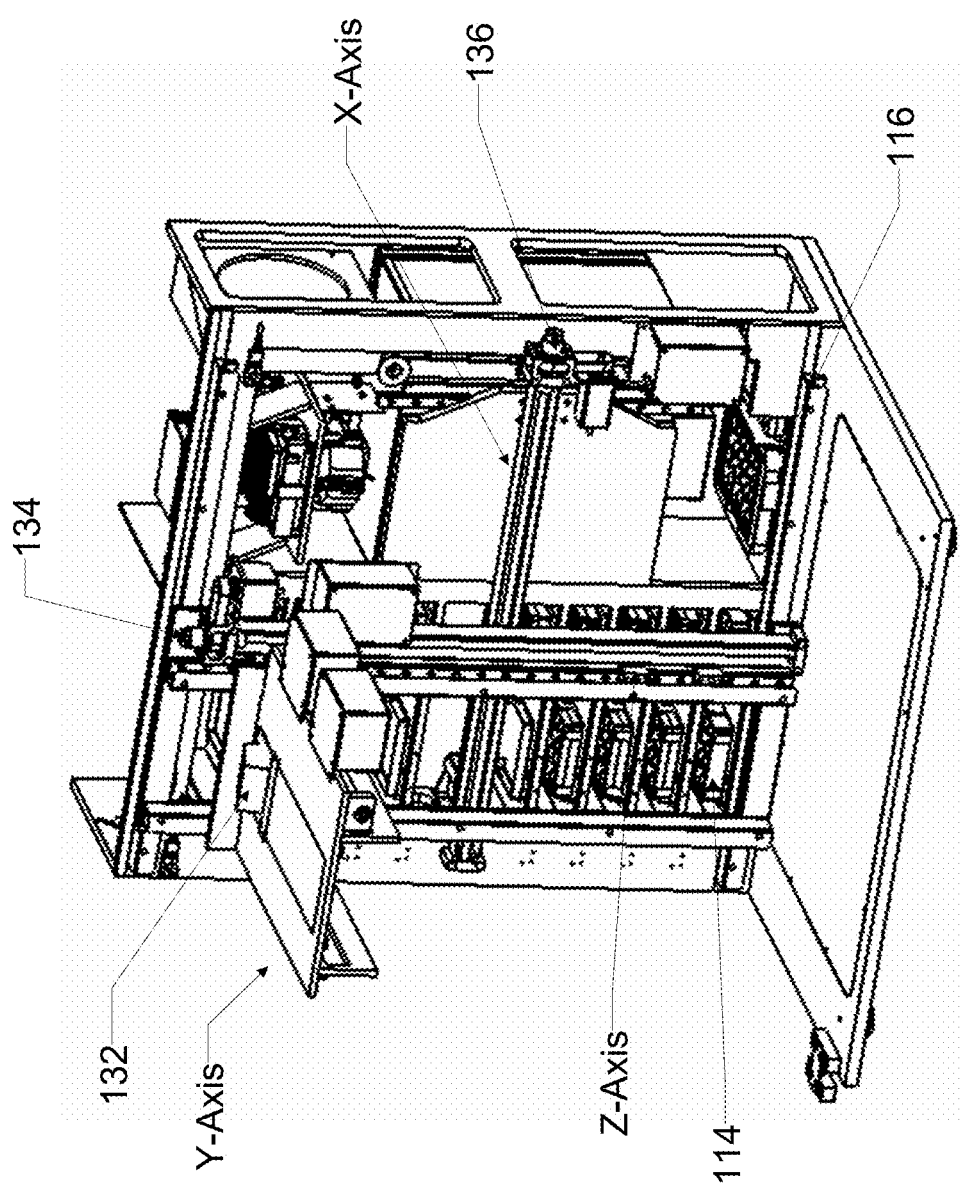

FIGS. 1-2 show a simplified system for processing biological sensors according to an embodiment of the present invention. These diagrams are merely examples, which should not unduly limit the scope of the claims. One of ordinary skill in the art would recognize many variations, alternatives, and modifications. The system 100 includes a fluidic component, a support component, and an electrical and mechanical component. Although the above has been shown using a selected group of components for the system 100, there can be many alternatives, modifications, and variations. For example, some of the components may be expanded and/or combined. Other components may be inserted to those noted above. Depending upon the embodiment, the arrangement of components may be interchanged with others replaced. For example, the system 100 is used, at least in part, as a fluidic station. Further details of these components are found throughout the present specification and more particularly below.

The fluidic component includes at least some containers. Each of these containers includes one or more fluids for processing at least one biological sensor. For example, each container is a well. In another example, the wells are grouped into one or more plate and/or one or more strip. As shown in FIGS. 1-2, the wells are grouped into at least one or more of well plates 112, 114, and 116. In one embodiment, each of the well plates 112, 114, and 116 includes 96 wells. In another embodiment, each well contains one or more fluids. In yet another embodiment, different wells of the same plate or different plates contain the same or different fluids. In yet another embodiment, different wells have the same or different depths.

According to one embodiment of the present invention, the fluidic component 110 also includes one or more holder plates. For example, each holder plate includes a plurality of wells arranged in a plurality of rows and a plurality of columns and capable of holding the one or more sensors. In one embodiment, a holder plate is used to transport the one or more sensors to the system 100 before or after a hybridization process is performed. In another embodiment, a holder plate is used to transport the one or more sensors out of the system 100. For example, the holder plate is a scan tray including at least a cuvette holder.

The support component includes at least a panel 140 and drawer assemblies 122, 124 and 128. For example, each of the drawer assemblies 122, 124, and 128 includes a panel, which can slide in the horizontal direction. In one embodiment, the well plate 112 is placed on the panel for the drawer assembly 122, and the well plate 124 is placed on the panel for the drawer assembly 124. For example, the well plate 112 is fixed at a predetermined position, directly or indirectly, on the panel for the drawer assembly 122. In another example, the one or more wells of the well plate 124 are substantially perpendicular to the panel for the drawer assembly 122.

As shown in FIGS. 1-2, the support component also includes additional drawer assemblies according to another embodiment of the present invention. Each of the additional drawer assemblies includes a panel, which can slide in the horizontal direction. In one embodiment, a well plate or a holder plate is placed on the panel. For example, the well plate or the holder plate is fixed at a predetermined position, directly or indirectly, on the panel. In another example, the one or more wells of the well plate or the holder plate are substantially perpendicular to the panel.

Additionally, the support component also includes a hot plate assembly 126. In one embodiment, the hot plate assembly 126 is placed on the panel for the drawer assembly 128. For example, the hot plate assembly 126 is fixed at a predetermined position, directly or indirectly, on the panel for the drawer assembly 128.

Figure 3A:
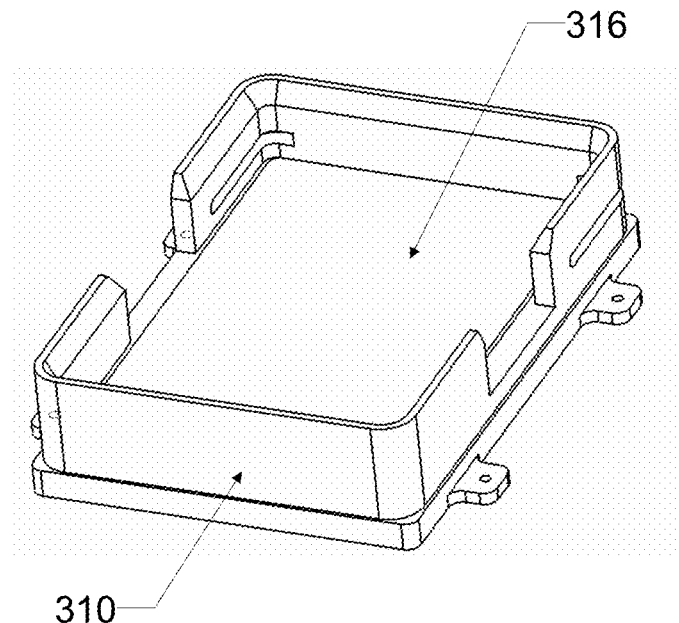
FIGS. 3(A) and (B) show a simplified hot plate assembly in system for processing biological sensors according to an embodiment of the present invention.
Figure 3B:
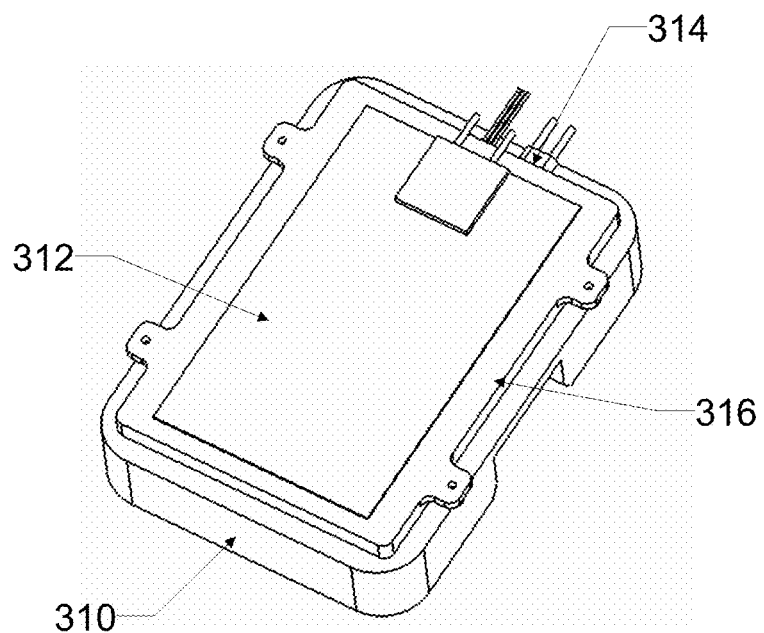

FIGS. 3(A) and (B) show a simplified hot plate assembly 126 in system 100 for processing biological sensors according to an embodiment of the present invention. These diagrams are merely examples, which should not unduly limit the scope of the claims. One of ordinary skill in the art would recognize many variations, alternatives, and modifications. The hot plate assembly 126 includes an insulation structure 310, a heater 312, a thermometer 314 such as a thermocouple, and a conduction structure 316. Although the above has been shown using a selected group of components for the hot plate assembly 126, there can be many alternatives, modifications, and variations. For example, some of the components may be expanded and/or combined. Other components may be inserted to those noted above. Depending upon the embodiment, the arrangement of components may be interchanged with others replaced. For example, FIG. 3(A) shows a simplified top view, and FIG. 3(B) shows a simplified bottom view. Further details of these components are found throughout the present specification and more particularly below.

As shown in FIGS. 1, 2, and 3(A) and (B), the well plate 116 is placed on the conduction structure 316 according to an embodiment of the present invention. For example, the well plate 116 includes one or more wells, and each well contains at least one fluid. The fluid is heated by the heater 312 through the conduction structure 316. The temperature of the fluid is monitored, directly or indirectly, by the thermocouple 314. In response, the thermocouple 314 sends a signal to a temperature controller. In one embodiment, the temperature controller is also a component of the system 100. The temperature controller processes the received signal in light of a target temperature and adjusts the power of the heater 312 in order to achieve the target temperature for the fluid. In one embodiment, the target temperature is provided to the system 100 by the user through a temperature interface. For example, the temperature interface is a component of the system 100. In another embodiment, the target temperature is provided to the system 100 by the well plate 116 itself. For example, the well plate 116 carries a barcode, which is read by a barcode reader for the system 100. Based on the barcode, the system 100 can determine the target temperature. In another example, the barcode reader, e.g., a detector, is a component of the system 100.

Returning to FIGS. 1-2, the electrical and mechanical component can move each of the one or more sensors from one position to another position. In one embodiment, the electrical and mechanical component is used as a transport component. In another embodiment, the movement of the sensors can be made in one, two, or three dimensions. In yet another embodiment, the movement of the sensors is made at various speed. As shown in FIGS. 1-2, the electrical and mechanical component moves each of the one or more sensors from one well to another well of the fluidic component. For example, each of the one or more sensors is moved from one well of the well plate 112 to another well of the well plate 114. Additionally, the electrical and mechanical component can move each of the one or more sensors within a corresponding well of the fluidic component 110, and/or move each of the one or more sensors into and/or out of a corresponding well of the fluidic component 110. For example, the corresponding well is a well of the well plate 112 or 114.

According to an embodiment of the present invention, the electrical and mechanical component includes a gripper assembly 132, and at least motors 134 and 136. The gripper assembly 132 can grip or release, directly or indirectly, one or more sensors. Each of the motors 134 and 136 can move the one or more gripped sensors in two opposite directions of one dimension. For example, the motor 134 can move the one or more sensors along the Z axis that is perpendicular to the panel of the drawer assembly 122 or 124. In another example, the motor 136 can move the one or more gripped sensors along the X axis that is parallel to the panel of the drawer assembly 122 or 124. Additionally, the electrical and mechanical component includes a third motor. For example, the third motor can move the one or more gripped sensors in two opposite directions along the Y axis as shown in FIGS. 1-2.

Figure 4A:
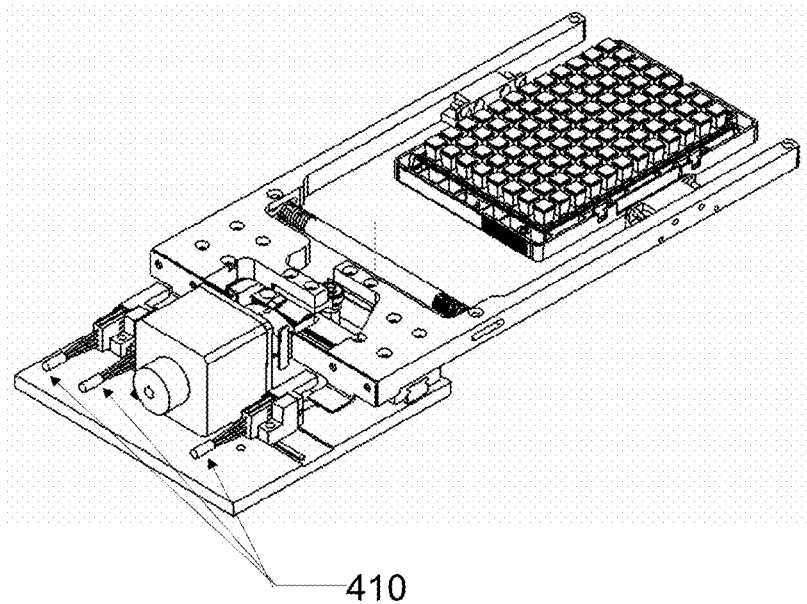
FIGS. 4(A) and (B) show a simplified gripper assembly in system for processing biological sensors according to an embodiment of the present invention.
Figure 4B:
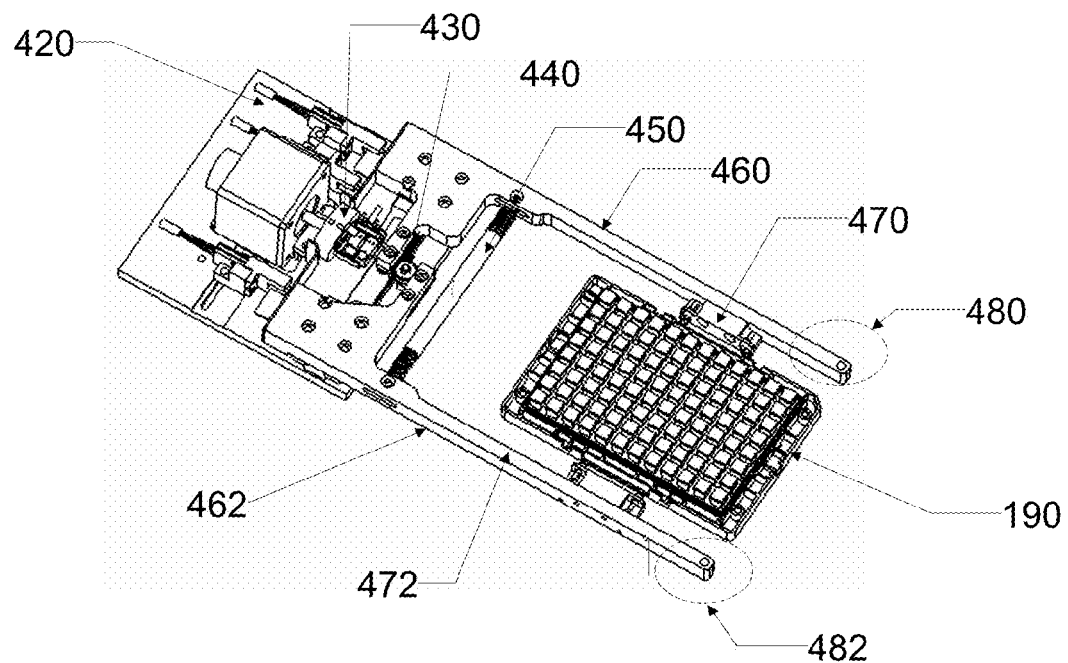

FIGS. 4(A) and (B) show a simplified gripper assembly 132 in system 100 for processing biological sensors according to an embodiment of the present invention. These diagrams are merely examples, which should not unduly limit the scope of the claims. One of ordinary skill in the art would recognize many variations, alternatives, and modifications. The gripper assembly 132 includes sensors 410, a motor 420, a cam 430, rack and pinion 440, a spring 450, arms 460 and 462, and finger assemblies 470 and 472. Although the above has been shown using a selected group of components for the gripper assembly 132, there can be many alternatives, modifications, and variations. For example, some of the components may be expanded and/or combined. Other components may be inserted to those noted above. Depending upon the embodiment, the arrangement of components may be interchanged with others replaced. Further details of these components are found throughout the present specification and more particularly below.

Each of the finger assemblies 470 and 472 includes one or more fingers, such as two fingers. When the fingers are in the closed position, the fingers can grip, directly or indirectly, the one or more sensors 190. When the fingers are in the open position, the fingers can release, directly or indirectly, the one or more sensors 190. As shown in FIGS. 4(A) and (B), the finger assemblies 470 and 472 are attached to the arms 460 and 462 respectively. The movement of the fingers between the closed position and the open position is driven by the motor 420. The motor 420 can apply force to the fingers through at least the cam 430 and the arms 460 and 462. In one embodiment, the arm 460 extends beyond the section used for attaching the finger assembly 470, and the arm 462 extends beyond the section used for attaching the finger assembly 472. For example, the arm 460 includes the segment 480, and the arm 462 includes the segment 482. In another example, the sensors 410 includes home and limit sensors.

Figure 5A:
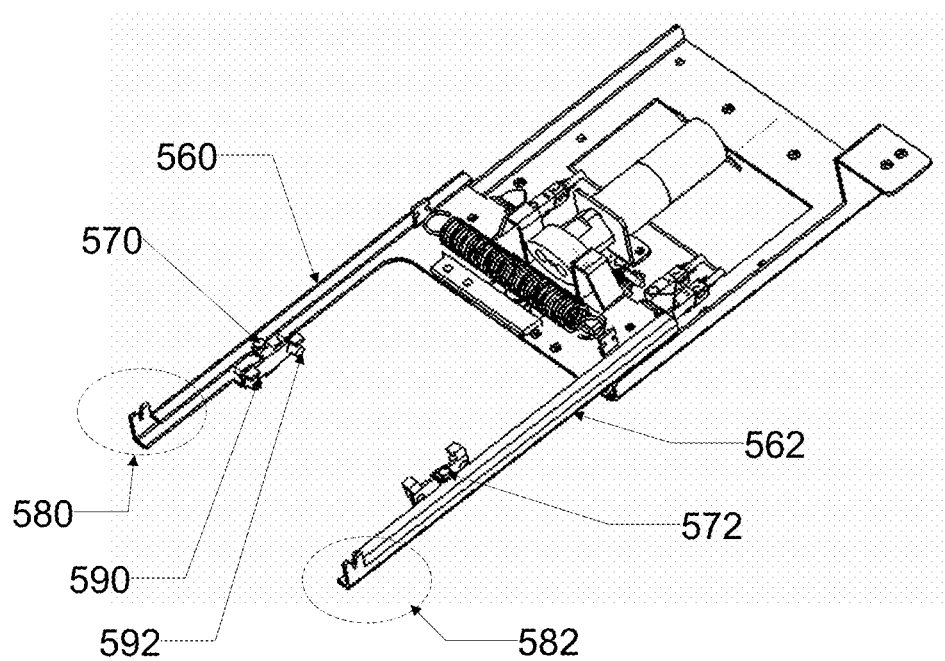
FIGS. 5(A) and (B) show a simplified gripper assembly in system for processing biological sensors according to another embodiment of the present invention.
Figure 5B:
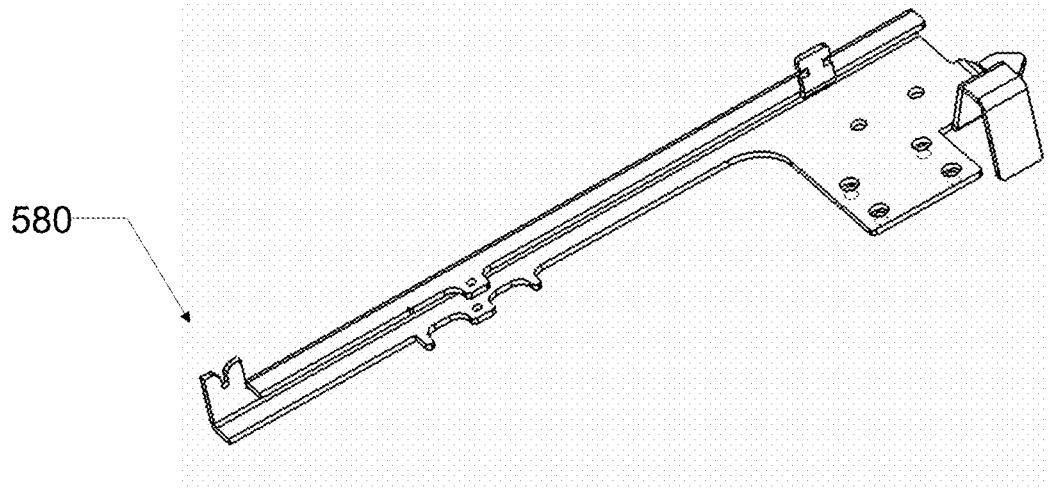

FIGS. 5(A) and (B) show a simplified gripper assembly 132 in system 100 for processing biological sensors according to another embodiment of the present invention. These diagrams are merely examples, which should not unduly limit the scope of the claims. One of ordinary skill in the art would recognize many variations, alternatives, and modifications. The gripper assembly 132 includes two arms 560 and 562. The two arms 560 and 562 are attached to the finger assemblies 570 and 572 respectively. The finger assembly 570 includes two fingers 590 and 592, and the finger assembly 572 also includes two fingers. When the fingers are in the closed position, the fingers can grip, directly or indirectly, the one or more sensors. When the fingers are in the open position, the fingers can release, directly or indirectly, the one or more sensors. In one embodiment, the arm 560 extends beyond the section used for attaching the finger assembly 570, and the arm 562 extends beyond the section used for attaching the finger assembly 572. For example, the arm 560 includes the segment 580, and the arm 562 includes the segment 582.

Returning to FIGS. 1-2, as discussed above, the electrical and mechanical component includes a gripper assembly 132, the motors 134 and 136, and the third motor. The gripper assembly 132 can grip or release, directly or indirectly, one or more sensors. Each of the motors can move the one or more gripped sensors in at least one direction of one dimension. Additionally, the third motor can also use the gripper assembly 132 to make a drawer assembly slide in two opposite directions. For example, the drawer assembly is the drawer assembly 122 or 124. In another example, the two opposite directions are horizontal.

The electrical and mechanical component includes other components in addition to the gripper assembly 132, and certain motors according to an embodiment of the present invention. For example, the electrical and mechanical component includes at least a high-voltage power supply and a low-voltage power supply. In one embodiment, the power suppliers are used to provide voltages at predetermined values and/or within predetermined ranges to, for example, the motors. In another embodiment, the power suppliers receive 115-voltage AC power from an external source.

Figure 6A:
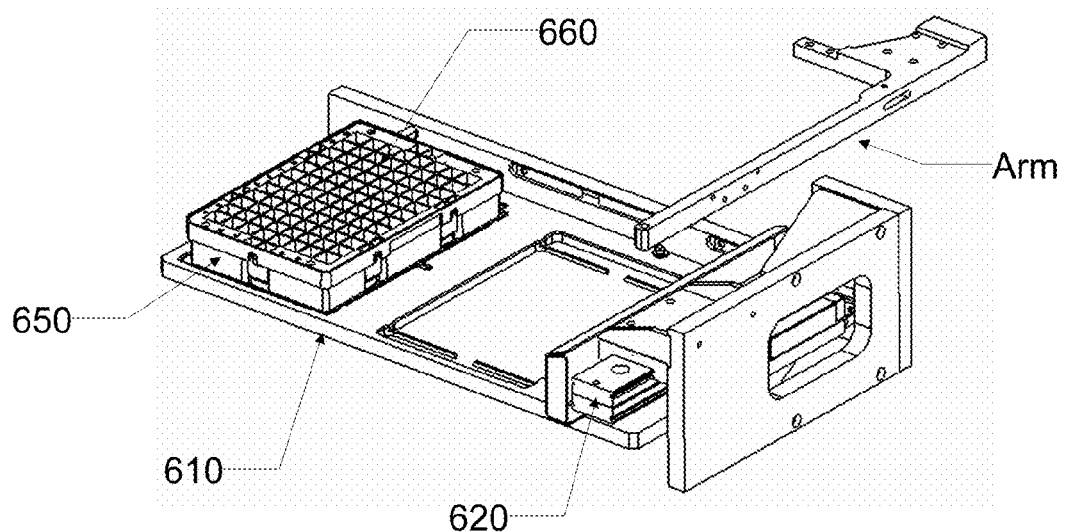
FIGS. 6(A) and (B) show a simplified drawer assembly in system for processing biological sensors according to an embodiment of the present invention.
Figure 6B:
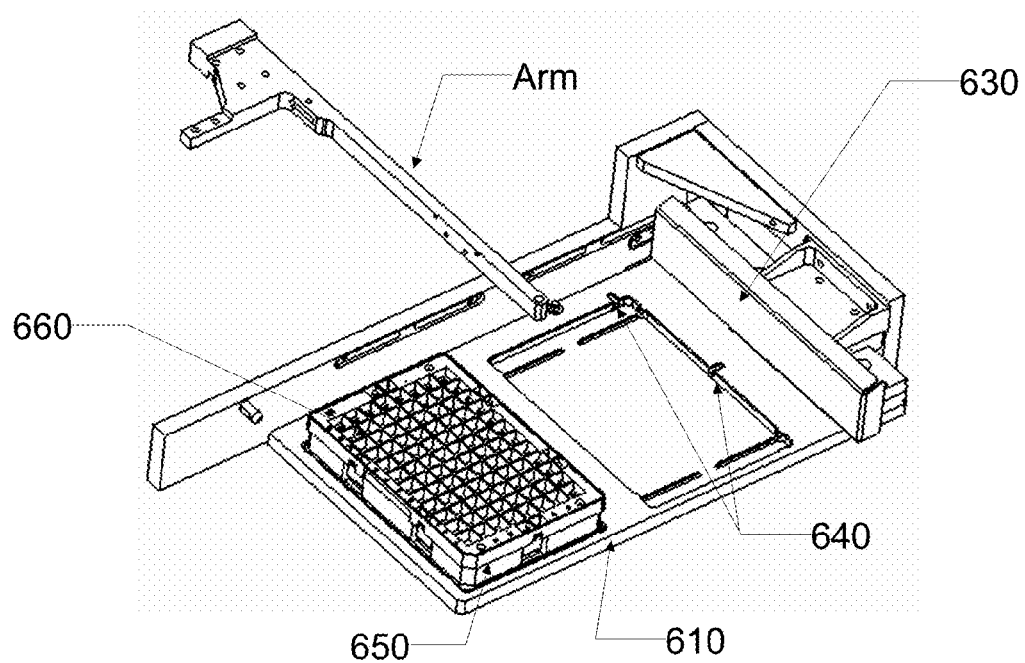

FIGS. 6(A) and (B) show a simplified drawer assembly 122 or 124 in system 100 for processing biological sensors according to an embodiment of the present invention. These diagrams are merely examples, which should not unduly limit the scope of the claims. One of ordinary skill in the art would recognize many variations, alternatives, and modifications. The drawer assembly includes a panel 610, a telescoping linear bearing 620, a splash guard 630, and plate biasing features 640.

As shown in FIGS. 6(A) and (B), the panel 610 includes one or more slots for supporting one or more well plates. For example, one slot is taken by a well plate 650, and the other slot remains empty. In one embodiment, the well plate 650 is at least partially covered by a plate for one or more sensors. In another embodiment, the well plate 650 is not at least partially covered by a plate for one or more sensors. The movement of the drawer assembly 122 or 124 is driven by a motor, such as the third motor of the gripper assembly 132, through at least one arm of the gripper assembly 132. For example, the at least one arm includes the arm 460 and/or the arm 462. In another example, the at least one arm includes the arm 560 and/or the arm 562.

Figure 7A:
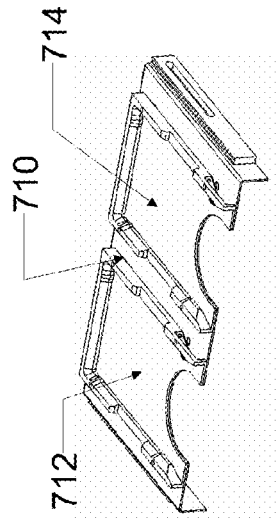
FIGS. 7(A), (B), and (C) show at least a simplified drawer assembly in system for processing biological sensors according to another embodiment of the present invention.
Figure 7C:
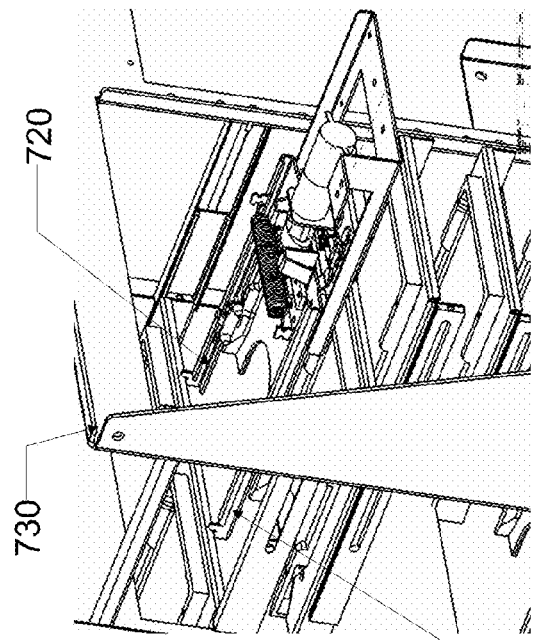

FIGS. 7(A), (B), and (C) show at least a simplified drawer assembly 122 or 124 in system 100 for processing biological sensors according to another embodiment of the present invention. These diagrams are merely examples, which should not unduly limit the scope of the claims. One of ordinary skill in the art would recognize many variations, alternatives, and modifications. The drawer assembly includes at least a panel 710 that includes slots 712 and 714. For example, both slots 712 and 714 remain empty.

Figure 7B:
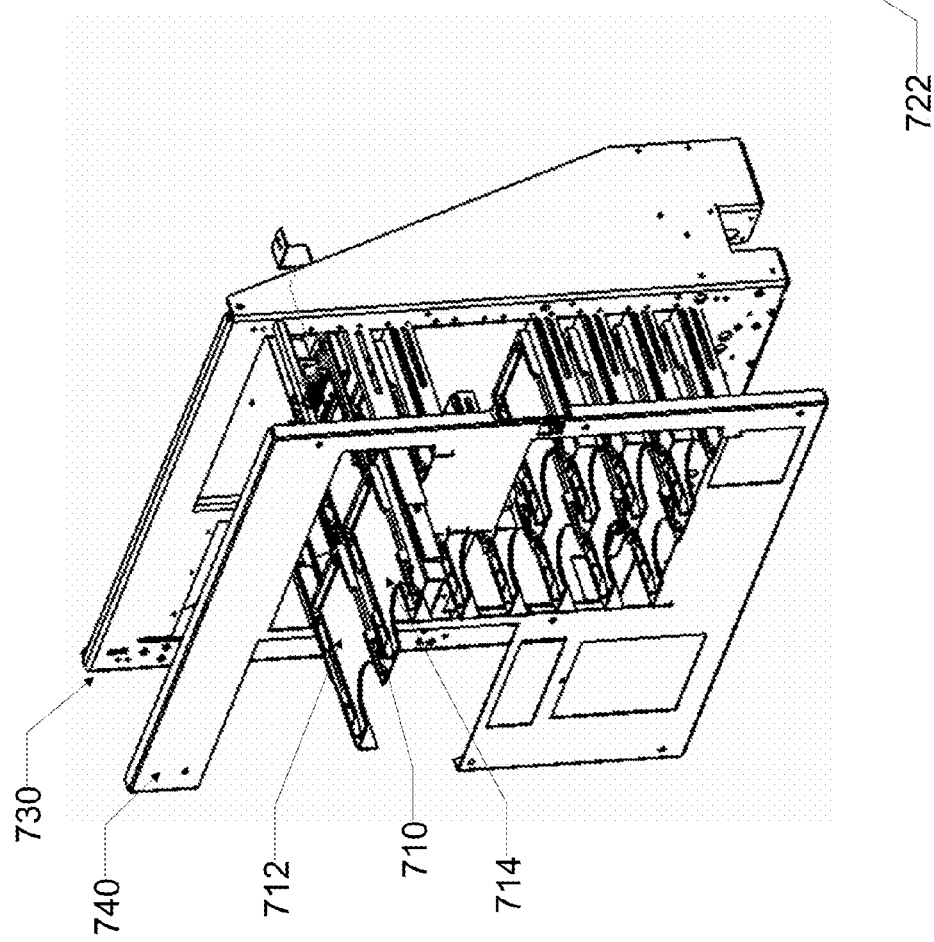

The movement of the drawer assembly 122 or 124 is driven, e.g., pushed or pulled, by a motor, such as the third motor of the gripper assembly 132, through arms 720 and 722. For example, the arms 720 and 722 are the arms 460 and 462. In another example, the arms 720 and 722 are the arms 560 and 562. As shown in FIGS. 7(B) and (C), the drawer assembly 122 or 124 is pushed from a closed position between panels 730 and 740 to an open position according to an embodiment of the present invention. For example, the panel 730 is the panel 140 as shown in FIG. 1. In another example, the panel 740 is a component of the system 100, but is not shown in FIG. 1. According to another embodiment, the drawer assembly 122 or 124 is pulled from the open position to the closed position. According to yet another embodiment, the movement of the drawer assembly 128 is driven, e.g., pushed or pulled, by a motor, such as the third motor of the gripper assembly 132 through its two arms.

Figure 8:
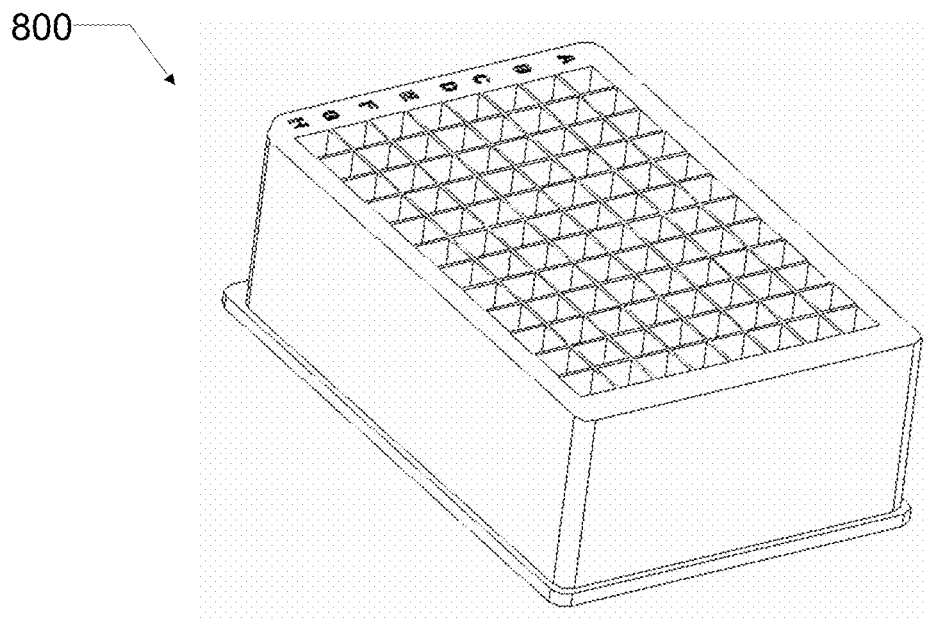
FIG. 8 shows a simplified well plate used in system for processing biological sensors according to an embodiment of the present invention.

FIG. 8 shows a simplified well plate used in system 100 for processing biological sensors according to an embodiment of the present invention. These diagrams are merely examples, which should not unduly limit the scope of the claims. One of ordinary skill in the art would recognize many variations, alternatives, and modifications. The well plate 800 includes a plurality of containers, such as 96 wells. In one embodiment, the plurality of containers are arranged into a plurality of rows and a plurality of columns. In another embodiment, each well contains one or more fluids. For example, the volume of the one or more fluids in each well is equal to or smaller than 3 ml or 5 ml. In one embodiment, the volume of the one or more fluids for low stringency wash or stain is about 1.9 ml, and for high stringency wash is about 3.7 ml. In another embodiment, different wells have the same or different depths. For example, the well plate 800 is used as the well plate 112, 114, and/or 116.

As discussed above and further emphasized here, the system 100 can be used to process biological sensors according to certain embodiments of the present invention. As an example, the biological sensors can be various types. See U.S. patent application Ser. No. 10/826,577 filed Apr. 16, 2004 and Ser. No. 11/243,621 filed Oct. 4, 2005, each of which is incorporated by reference herein. In another example, each of the one or more biological sensors is a biological microarray. In one embodiment, the biological microarray has a sensor length, a sensor width, and a sensor thickness. For example, the sensor length is equal to or shorter than 10 mm, the sensor width is equal to or narrower than 10 mm, and the sensor thickness is equal to or thinner than 1000 μm. In another example, the sensor length is equal to about 6.3 mm, the sensor width is equal to about 6.3 mm, and the sensor thickness is equal to about 700 μm.

Figure 9:
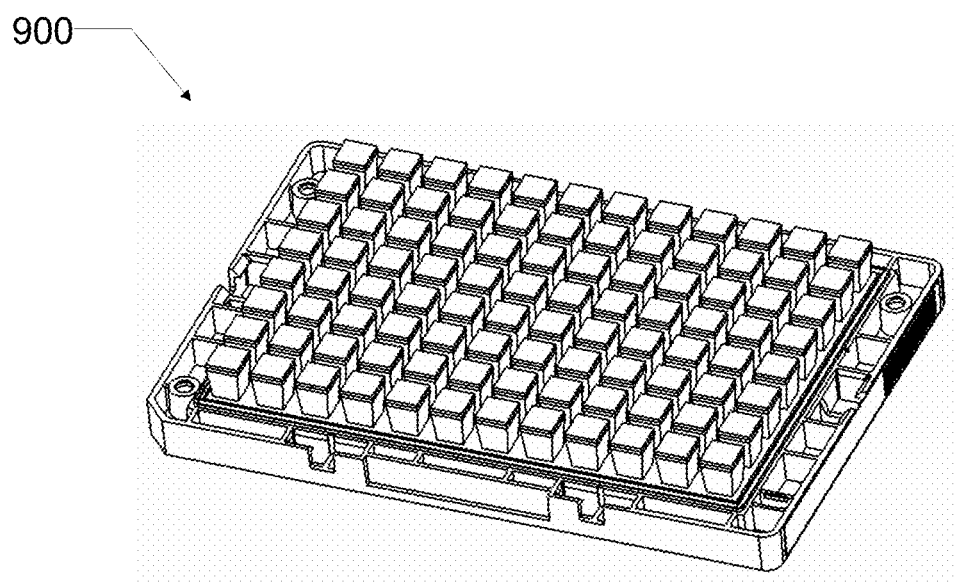
FIG. 9 is a simplified sensor assembly that can be processed by system according to an embodiment of the present invention.

According to one embodiment of the present invention, each of the one or more biological sensors is attached to a support component. For example, the support component is a peg. FIG. 9 is a simplified sensor assembly that can be processed by system 100 according to an embodiment of the present invention. This diagram is merely an example, which should not unduly limit the scope of the claims. One of ordinary skill in the art would recognize many variations, alternatives, and modifications. As shown in FIG. 9, the sensor assembly 900 includes a plurality of biological microarrays, a plurality of pegs, and a base component. The plurality of biological microarrays is attached to the plurality of pegs respectively, and the plurality of pegs is connected by the base component. For example, the plurality of pegs includes 96 pegs, and the plurality of biological microarrays includes 96 microarrays. In another example, the plurality of microarrays is manipulated together by the system 100.

Figure 10:
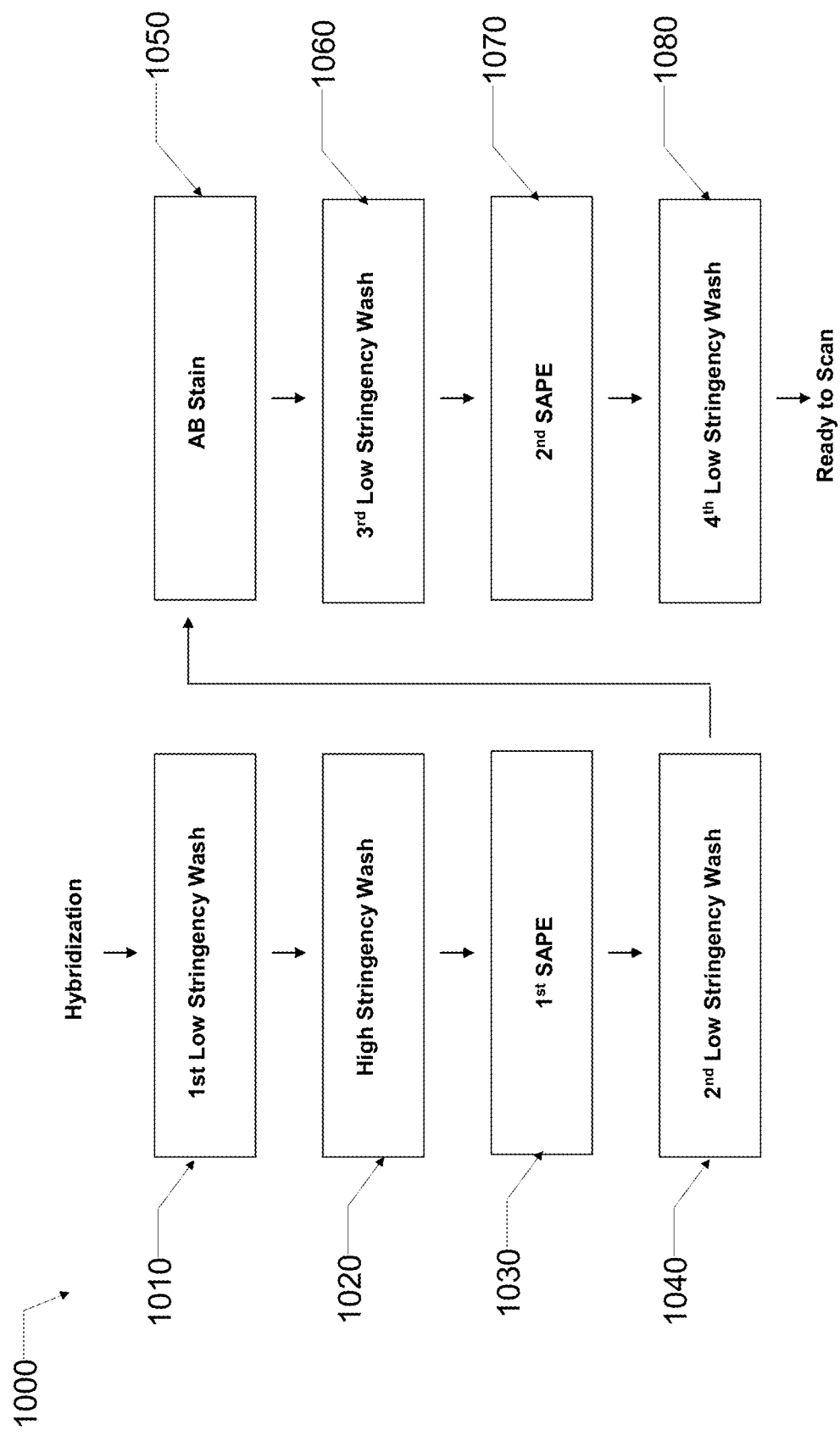
FIG. 10 shows a simplified fluidic method for processing biological sensors that is performed by system according to an embodiment of the present invention.

FIG. 10 shows a simplified fluidic method for processing biological sensors that is performed by system 100 according to an embodiment of the present invention. This diagram is merely an example, which should not unduly limit the scope of the claims. One of ordinary skill in the art would recognize many variations, alternatives, and modifications. The method 1000 includes a process 1010 for low stringency wash, a process 1020 for high stringency wash, a process 1030 for Streptavidin Phycoerythrin (SAPE) stain, a process 1040 for low stringency wash, a process 1050 for antibody (AB) stain, a process 1060 for low stringency wash, a process 1070 for SAPE stain, and a process 1080 for low stringency wash. Although the above has been shown using a selected sequence of processes, there can be many alternatives, modifications, and variations. For example, some of the processes may be expanded and/or combined. Other processes may be inserted to those noted above. Depending upon the embodiment, the specific sequence of processes may be interchanged with others replaced. Further details of these processes are found throughout the present specification and more particularly below.

At each of the processes 1010, 1040, and 1060 for low stringency wash, each of the one or more sensors is washed in a plurality of wells at room temperature. For example, the plurality of wells includes 2 wells. In another example, the plurality of wells includes 4 wells. For each well, the corresponding sensor is mixed with the fluid in the well for a plurality of times, such as under control of the gripper assembly 132. For example, the plurality of times includes 23 times within 3 minutes. In another example, the plurality of times includes 36 times within 2 minutes.

At the process 1020 for high stringency wash, each of the one or more sensors is washed in at least one well. Within each well, the fluid is at an elevated temperature, and the corresponding sensor is mixed with the fluid for a period of time. For example, the elevated temperature is 48° C., and the period of time is 25 minutes. In another example, the elevated temperature ranges from 36 to 42° C., such as 41° C., and the period of time is also 25 minutes.

At each of the processes 1030 and 1070 for SAPE stain, each of the one or more sensors is stained in at least one well at room temperature. For each well, the corresponding sensor is mixed with the fluid for a period of time. As an example, example, the period of time is 10 minutes. At the process 1050 for AB stain, each of the one or more sensors is stained in at least one well at room temperature. For each well, the corresponding sensor is mixed with the fluid for a period of time. As an example, the period of time is 10 minutes.

As discussed above and further emphasized here, the processes 1010, 1020, 1030, 1040, 1050, 1060, 1070, and 1080 are all performed by the system 100 according to an embodiment of the present invention. Prior to the process 1010, the one or more sensors are processed for hybridization. For example, the hybridization process is performed at a temperature ranging from 48 to 52° C., such as 48° C., for 16 hours. Following the process 1080, the one or more sensors are scanned.

Figure 11A:
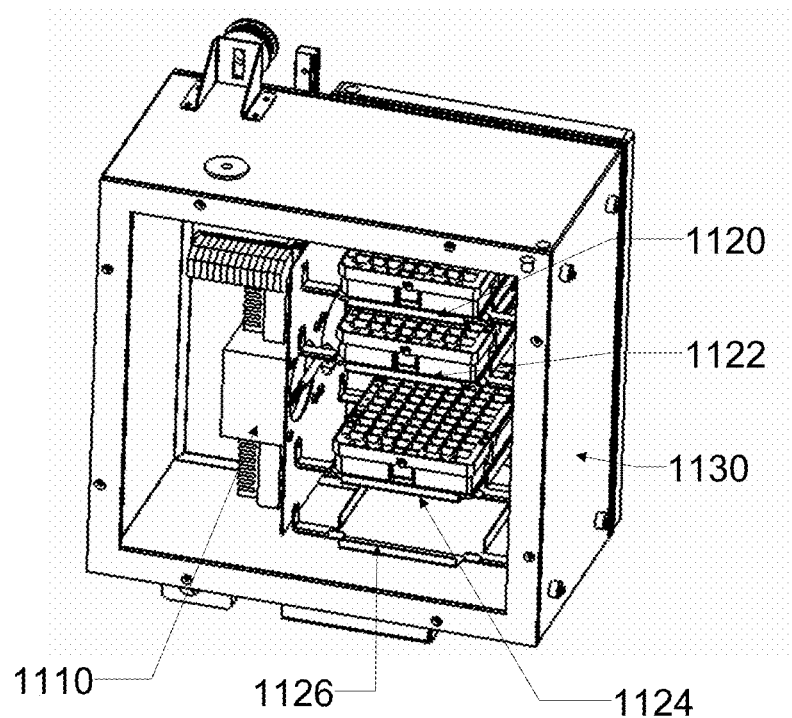
FIGS. 11(A) and (B) show a simplified oven assembly in system for processing biological sensors according to an embodiment of the present invention.
Figure 11B:
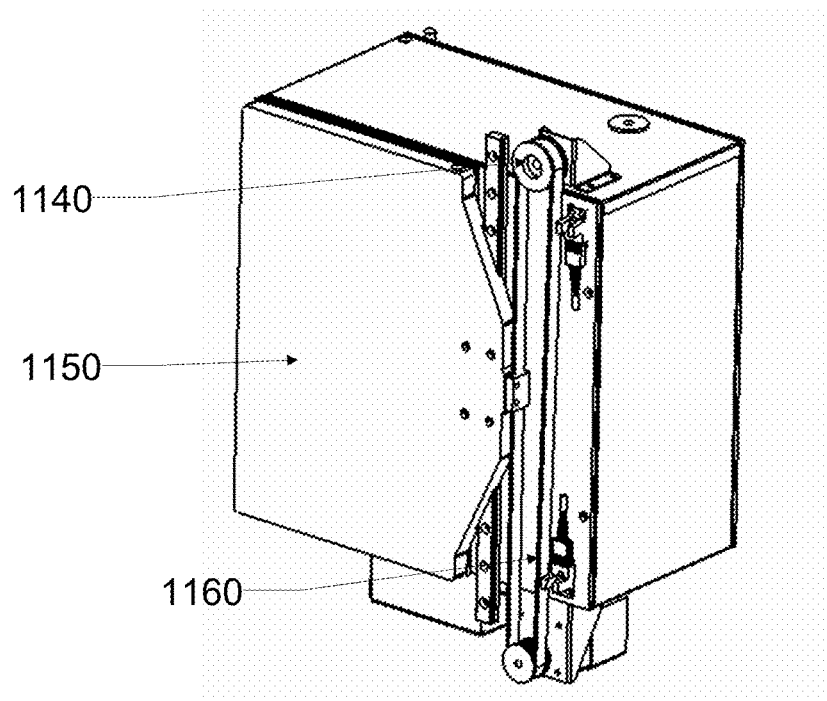
Figure 12:
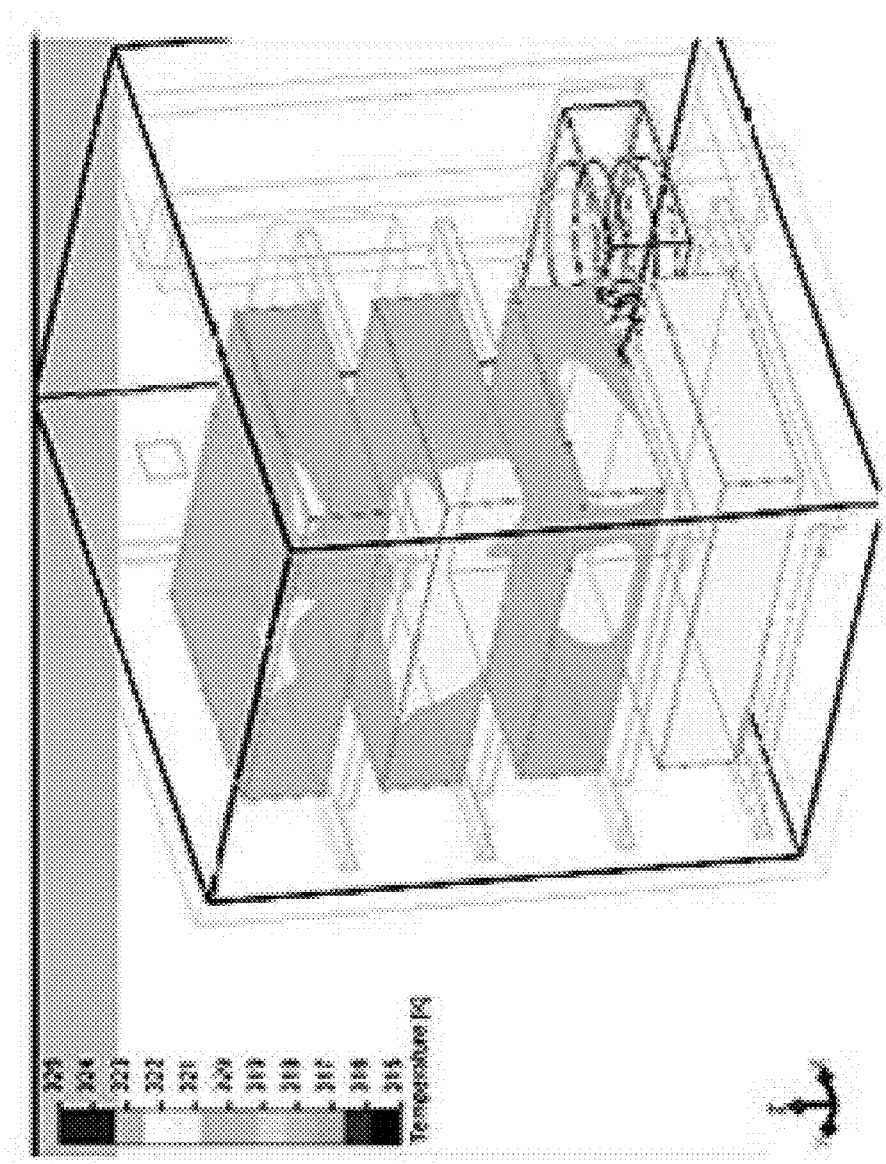
FIG. 12 is a simplified diagram showing temperature in tray vicinity for oven assembly in system for processing biological sensors according to an embodiment of the present invention.

Returning to FIGS. 1-2, the system 100 also includes an oven assembly 150 and an unclamping station 160. For example, the oven assembly 150 is used as at least a part of a hybridization component. Certain embodiments of the oven assembly 150 are shown in FIGS. 11(A), 11(B), and 12. Some embodiments of the unclamping station 160 is shown in FIGS. 13(A) and (B).

FIGS. 11(A) and (B) show a simplified oven assembly 150 in system 100 for processing biological sensors according to an embodiment of the present invention. These diagrams are merely examples, which should not unduly limit the scope of the claims. One of ordinary skill in the art would recognize many variations, alternatives, and modifications. The oven assembly 150 includes heater and fan 1110, panels 1120, 1122, 1124, and 1126, one or more walls 1130, belt and pulley 1140, a sliding door 1150, and sensors 1160 such as limit sensors. Although the above has been shown using a selected group of components for the gripper assembly 132, there can be many alternatives, modifications, and variations. For example, some of the components may be expanded and/or combined. Other components may be inserted to those noted above. Depending upon the embodiment, the arrangement of components may be interchanged with others replaced. For example, FIG. 11(A) shows a simplified front view, and FIG. 11(B) shows a simplified rear view. Further details of these components are found throughout the present specification and more particularly below.

The heater and fan 1110 can heat up the air and make the heated air circulate inside the oven assembly 150. The panels 1120, 1122, 1124, and 1126 each can support a holder plate, such as the holder plate is a hybridization tray. For example, the hybridization tray is clamped together with a sensor carrier with one or more sensors. In another example, the sensor carrier is the sensor assembly 900. The holder plate and the sensor carrier can be transported into or out of the oven assembly 150 by the gripper assembly 132. For example, the sliding door 1150 is open and the gripper assembly 132 moves three pairs of a holder plate and a sensor carrier into the oven assembly 1150, and places the three pairs on the panels 1120, 1122, and 1124 respectively. Afterwards, the sliding door is closed, and the oven assembly is heated. In another example, the movement of the sliding door is controlled at least in part by the belt and pulley 1140. Regardless of the number of the holder plates and the sensor carriers and their locations in the oven assembly, the oven assembly can provide uniform airflow according to an embodiment of the present invention. For example, aerogel insulation is used. In another example, one or more high-performance fans are used.

FIG. 12 is a simplified diagram showing temperature in tray vicinity for oven assembly 150 in system 100 for processing biological sensors according to an embodiment of the present invention. This diagram is merely an example, which should not unduly limit the scope of the claims. One of ordinary skill in the art would recognize many variations, alternatives, and modifications. For example, the air temperature in tray vicinity has a variation within +/−1.2° C. In another example, each tray is a hybridization tray. In yet another example, the temperature inside each tray should be more uniform due to conduction in the tray.

Figure 13:
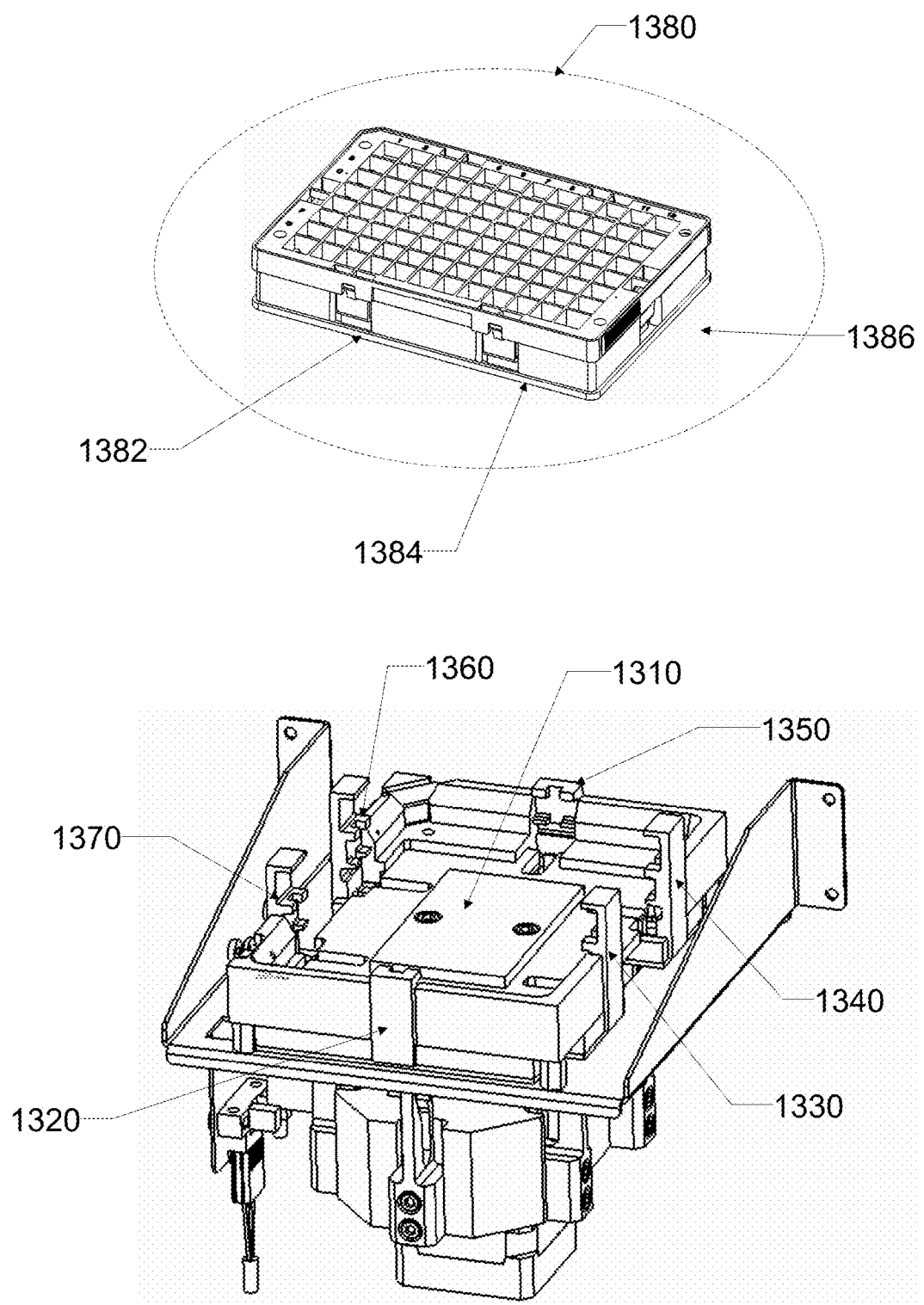
FIG. 13 shows a simplified unclamping station in system for processing biological sensors according to an embodiment of the present invention.

FIG. 13 shows a simplified unclamping station 160 in system 100 for processing biological sensors according to an embodiment of the present invention. This diagram is merely an example, which should not unduly limit the scope of the claims. One of ordinary skill in the art would recognize many variations, alternatives, and modifications. As shown in FIG. 13, the unclamping station 160 includes at least a panel 1310, and a plurality of finger assemblies. For example, the plurality of finger assemblies includes finger assemblies 1320, 1330, 1340, 1350, 1360, and 1370. In another example, a clamped assembly 1380 includes a holder plate and a sensor carrier. According to one embodiment, the holder plate is a hybridization tray, and the sensor carrier is the sensor assembly 900. According to another embodiment, the clamped assembly 1380 includes six handles, such as handles 1382, 1384, 1386, etc.

For example, the clamped assembly 1380 is placed onto the panel 1310 by the gripper assembly 132. On the panel 1310, the six handles matches with the six finger assemblies. The six finger assemblies are powered by an actuator in order to unclamp the holder plate and the sensor carrier. In one embodiment, the actuator is an electrical actuator. In another embodiment, the actuator is a pneumatic actuator. For example, the pneumatic actuator receives a gas at a first pressure from a gas regulator, and the gas regulator converts the gas at a second pressure to the gas at the first pressure. In another example, the gas is clean dry air.

As shown in FIGS. 1-2, the oven assembly 150 can be used to perform a hybridization process. For example, one or more clamped assemblies, each including a holder plate and a sensor carrier, are transported into the oven assembly 150 and placed onto the one or more panels respectively. Afterwards, the sliding door 1150 is closed, and the hybridization process is performed under one or more predetermined conditions. For example, the one or more predetermined conditions include a processing temperature that ranges from 48 to 52° C., such as 48° C., and a processing time that is equal to, for example, about 16 hours. After the hybridization process is completed, the sliding door is open, and at least one clamped assembly is moved from the oven assembly 150 to the unclamping station 160 by the gripper assembly 132. At the unclamping station 160, the sensor carrier is separated from the holder plate. Subsequently, the sensor carrier is transported by the griper assembly 132 to another location in order to perform the process 1010 and other processes of the method 1000.

As discussed above and further emphasized here, FIGS. 1-8 are merely examples, which should not unduly limit the scope of the claims. One of ordinary skill in the art would recognize many variations, alternatives, and modifications. For example, one or more of the well plates can be replaced by one or more well strips, each of which includes a single row or a single column. In another example, one or more of the holder plates can be replaced by one or more holder strips, each of which includes a single row or a single column. In yet another example, one or more additional well plates, and/or one or more additional holder plates can be included in the fluidic component of the system 100.

As shown in FIGS. 1-2, the fluidic component of the system 100 includes a plurality of slots for holding a plurality of plates, such as a well plate and/or a holder plate, according to an embodiment of the present invention. The plurality of plates can be used for performing the method 1000 with various configurations. At a given time, the number of the plurality of plates that are covered by a sensor carrier varies depending on different applications. For example, there is no plates in the slots that are covered by the sensor carrier. In another example, there is only plate outside the oven assembly 150 that is covered by the sensor carrier. In yet another example, there is more than one plate outside the over assembly 150 that are covered by the sensor carrier.

Figure 14:
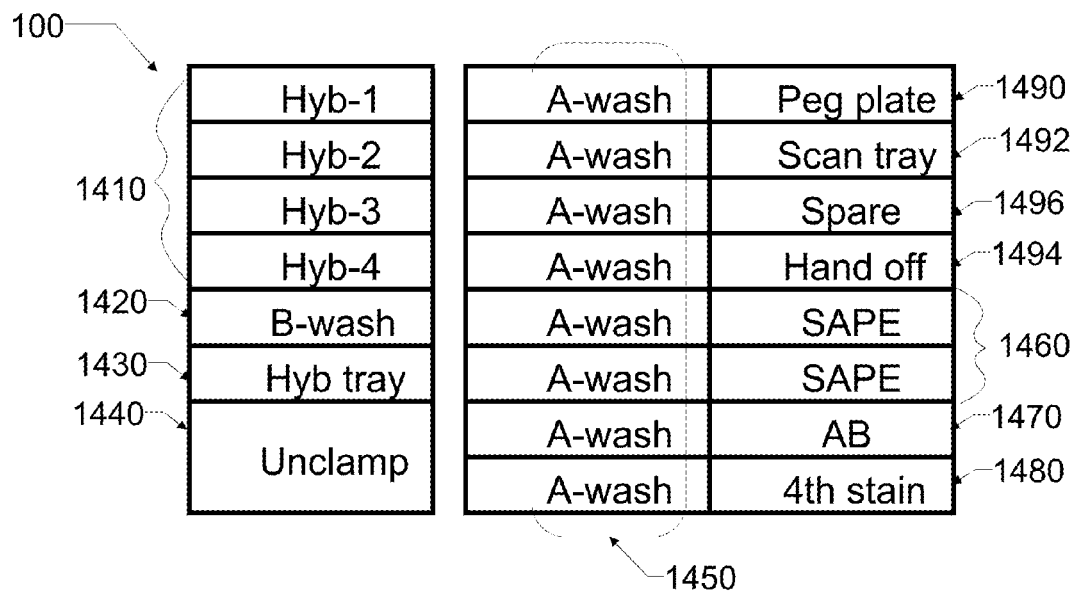
FIG. 14 shows a simplified configuration for system for processing biological sensors according to an embodiment of the present invention.

FIG. 14 shows a simplified configuration for system 100 for processing biological sensors according to an embodiment of the present invention. This diagram is merely an example, which should not unduly limit the scope of the claims. One of ordinary skill in the art would recognize many variations, alternatives, and modifications. The system 100 includes slots for holding various types of plates. For example, slots 1410 are parts of an oven assembly, such as the oven assembly 150. A slot 1420 is used for high-stringency wash including a hot plate assembly, such as the hot plate assembly 126. A slot 1430 is used for holding a holder plate, such as a hybridization tray. A slot 1440 is used as an unclamping station, such as the unclamping station 160. A plurality of slots 1450 are used for low-stringency wash. Moreover, slots 1460 are used for SAPE stain, a slot 1470 is used for AB stain, and a slot 1480 is used for additional stain.

A slot 1490 is used for holding the sensor carrier, such as the sensor assembly 900. For example, the gripper 132 moves a sensor carrier from the slot 1490 to the slot 1430, and at the slot 1430, the sensor carrier is clamped to the holder plate. In another example, the gripper 132 then moves the sensor carrier and the holder plate into at least one of the slots 1410 of the oven assembly. A slot 1492 is used for holding a holder plate, such as a scan tray including at least a cuvette holder. For example, the gripper 132 moves a sensor carrier to the slot 1492, and at the slot 1492, the sensor carrier is placed onto the holder plate.

Additionally, a slot 1494 is used for handoff with another system. For example, the gripper 132 moves one or more sensors to the slot 1494. In another example, from the slot 1494, the one or more sensors are transferred to another system. In one embodiment, the another system is a scanner system. In another embodiment, the transfer is performed manually or automatically. For example, the one or more sensors are removed from the slot 1494 by a user. In another example, the one or more sensors are removed from the slot 1494 by a mechanical arm or a load tray. In yet another example, the one or more sensors are transferred, manually or automatically, from another system to the slot 1494. In one embodiment, the another system is a scanner system. In another embodiment, the gripper 132 moves the one or more sensors from the slot 1494, directly or indirectly, to the slot 1492. Moreover, a slot 1496 is a spare slot for additional processing.

Figure 15:
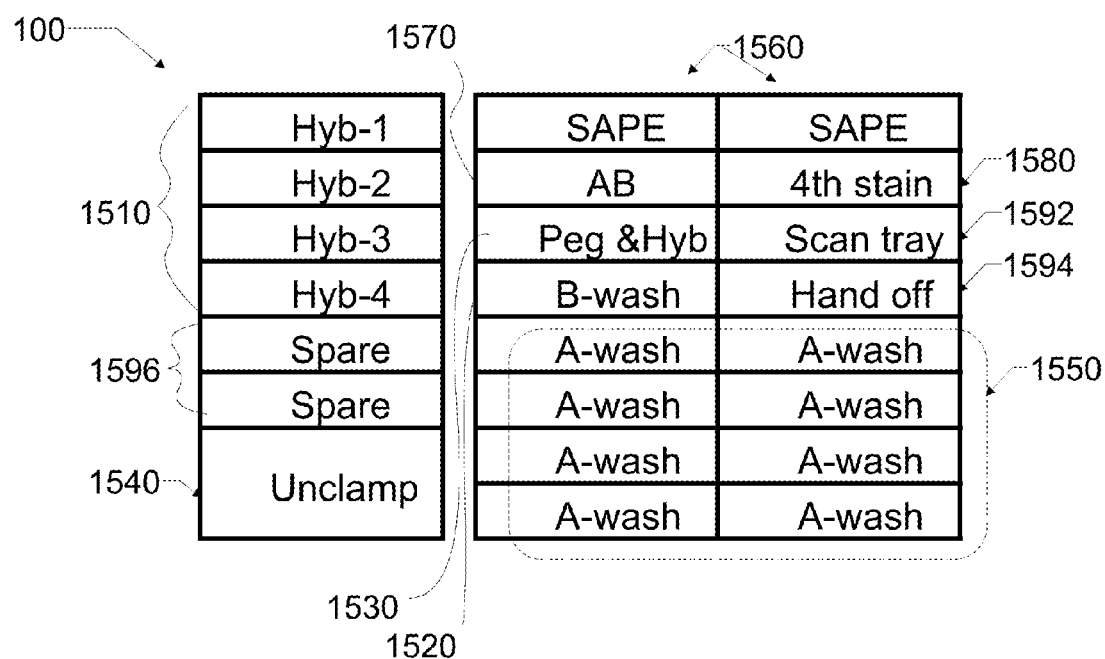
FIG. 15 shows a simplified configuration for system for processing biological sensors according to another embodiment of the present invention.

FIG. 15 shows a simplified configuration for system 100 for processing biological sensors according to another embodiment of the present invention. This diagram is merely an example, which should not unduly limit the scope of the claims. One of ordinary skill in the art would recognize many variations, alternatives, and modifications. The system 100 includes slots for holding various types of plates. For example, slots 1510 are parts of an oven assembly, such as the oven assembly 150. A slot 1520 is used for high-stringency wash including a hot plate assembly, such as the hot plate assembly 126. A slot 1530 is used for holding a holder plate clamped to a sensor carrier. For example, the holding plate is a hybridization tray. In another example, the sensor carrier is the sensor assembly 900. Additionally, a slot 1540 is used as an unclamping station, such as the unclamping station 160. A plurality of slots 1550 are used for low-stringency wash. Moreover, slots 1560 are used for SAPE stain, a slot 1570 is used for AB stain, and a slot 1580 is used for additional stain. A slot 1592 is used for holding a holder plate, such as a scan tray including at least a cuvette holder.

Additionally, a slot 1594 is used for handoff with another system. For example, the gripper 132 moves one or more sensors to the slot 1494. In another example, from the slot 1494, the one or more sensors are transferred to another system. In one embodiment, the transfer is performed manually or automatically. For example, the one or more sensors are removed from the slot 1494 by a user. In another embodiment, the one or more sensors are removed from the slot 1494 by a mechanical arm or a load tray. In yet another embodiment, the another system is a scanner system. Moreover, slots 1596 is spare slots for additional processing.

As shown in FIGS. 1-2 and 14-15, the gripper assembly 132 transports one or more clamped assemblies, each including a holder plate and a sensor carrier, into the oven assembly 150 and placed onto the one or more panels respectively. Afterwards, the sliding door 1150 is closed, and the hybridization process is performed under one or more predetermined conditions. After the hybridization process is completed, the sliding door is open, and at least one clamped assembly is moved from the oven assembly 150 to the unclamping station 160 by the gripper assembly 132. At the unclamping station 160, the sensor carrier is separated from the holder plate. Subsequently, the sensor carrier is transported by the gripper assembly 132 to another location in order to perform the process 1010 and other processes of the method 1000.

At each of the processes 1010, 1040, and 1060 for low stringency wash, the sensor carrier is moved to a slot for low stringency wash by the gripper assembly 132. Within the slot, the one or more sensors of the sensor carrier each are washed in a well of a well plate in the same slot. Afterwards, the sensor carrier is transported to one or more additional slots for low stringency wash.

At the process 1020 for high stringency wash, the sensor carrier is moved to a hot plate assembly, such as the hot plate assembly 126, by the gripper assembly 132. For example, the sensor carrier is placed in contact with the well plate on the conduction structure 316. Within each well of the well plate, the fluid is at an elevated temperature, and the corresponding sensor is mixed with the fluid for a period of time.

At each of the processes 1030 and 1070 for SAPE stain, the sensor carrier is transported to a slot for SAPE stain by the gripper assembly 132. Each of the one or more sensors is stained in at least one well at room temperature. For each well, the corresponding sensor is mixed with the fluid for a period of time. At the process 1050 for AB stain, the sensor carrier is moved to a slot for AB stain by the gripper assembly 132. Each of the one or more sensors is stained in at least one well at room temperature. For each well, the corresponding sensor is mixed with the fluid for a period of time.

According to one embodiment of the present invention, the movement of the one or more sensors into, within, and/or out of the system 100 is controlled by instructions received by the electrical and mechanical component from a processing system. For example, the processing system is external to the system 100. In another example, the processing system is a component of the system 100. In one embodiment, the processing system includes a computer or a processor. For example, the computer or the processor is directed by a code. In another example, the computer or the processor is directed by instructions included by a computer-readable medium in a computer program product.

As discussed above and further emphasized here, the system 100 can be used to process biological sensors ready for scan, such as following the process 1080, according to certain embodiments of the present invention. In one embodiment, the scanner for scanning the processed biological sensors can be of various types. For example, the scanner is made by Axon. Alternatively, see U.S. Provisional Application Ser. Nos. 60/648,309 filed Jan. 27, 2005 and 60/673,969 filed Apr. 22, 2005, each of which is incorporated by reference herein. In yet another example, the scanner for scanning the processed biological sensors is the scanner 1600 as shown in FIGS. 16(A) and (B), FIG. 17, and FIGS. 18(A)-(G), and FIGS. 19-21.

Figure 16A:
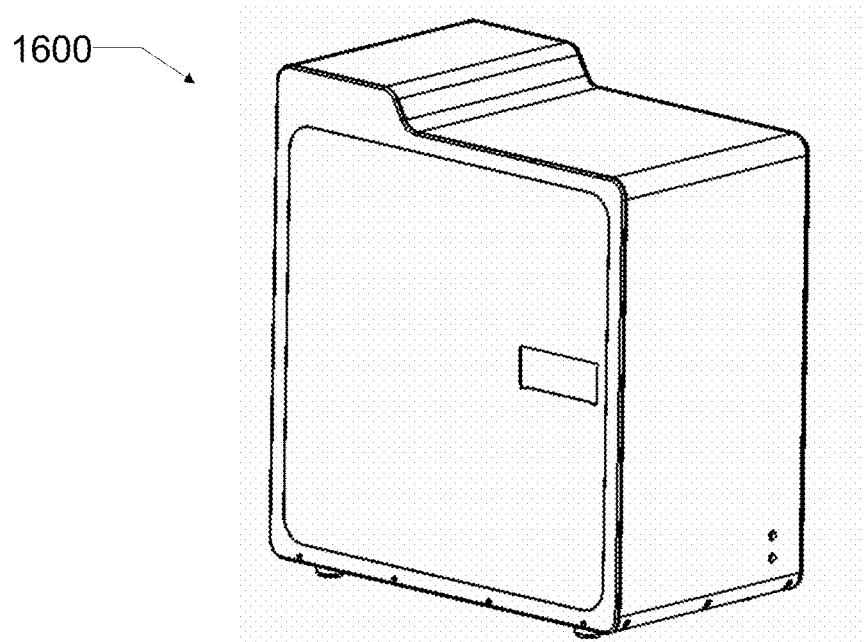
FIGS. 16(A) and (B) show a simplified scanner system that can be used with system for processing biological sensors according to an embodiment of the present invention.
Figure 16B:
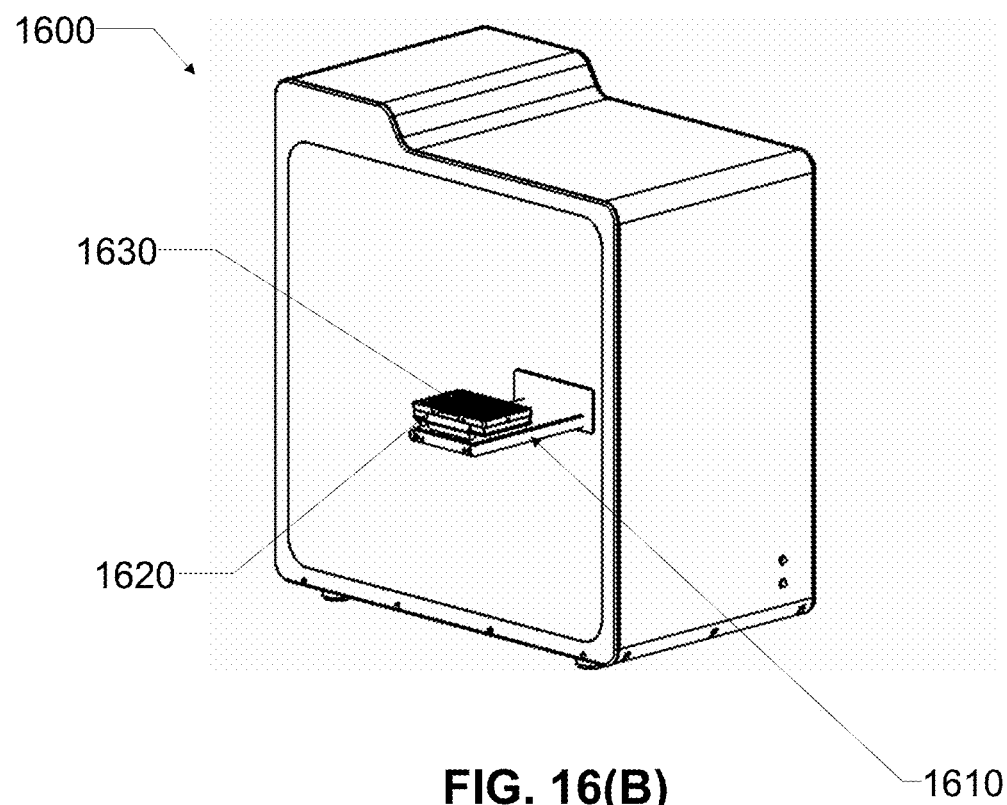

FIGS. 16(A) and (B) show a simplified scanner system that can be used with system 100 for processing biological sensors according to an embodiment of the present invention. These diagrams are merely examples, which should not unduly limit the scope of the claims. One of ordinary skill in the art would recognize many variations, alternatives, and modifications. The scanner system 1600 includes a loading tray 1610. The loading try 1610 can be extended to accept a sensor carrier 1630 on a well plate 1620, such as the sensor assembly 900 on the scan tray.

Figure 17:
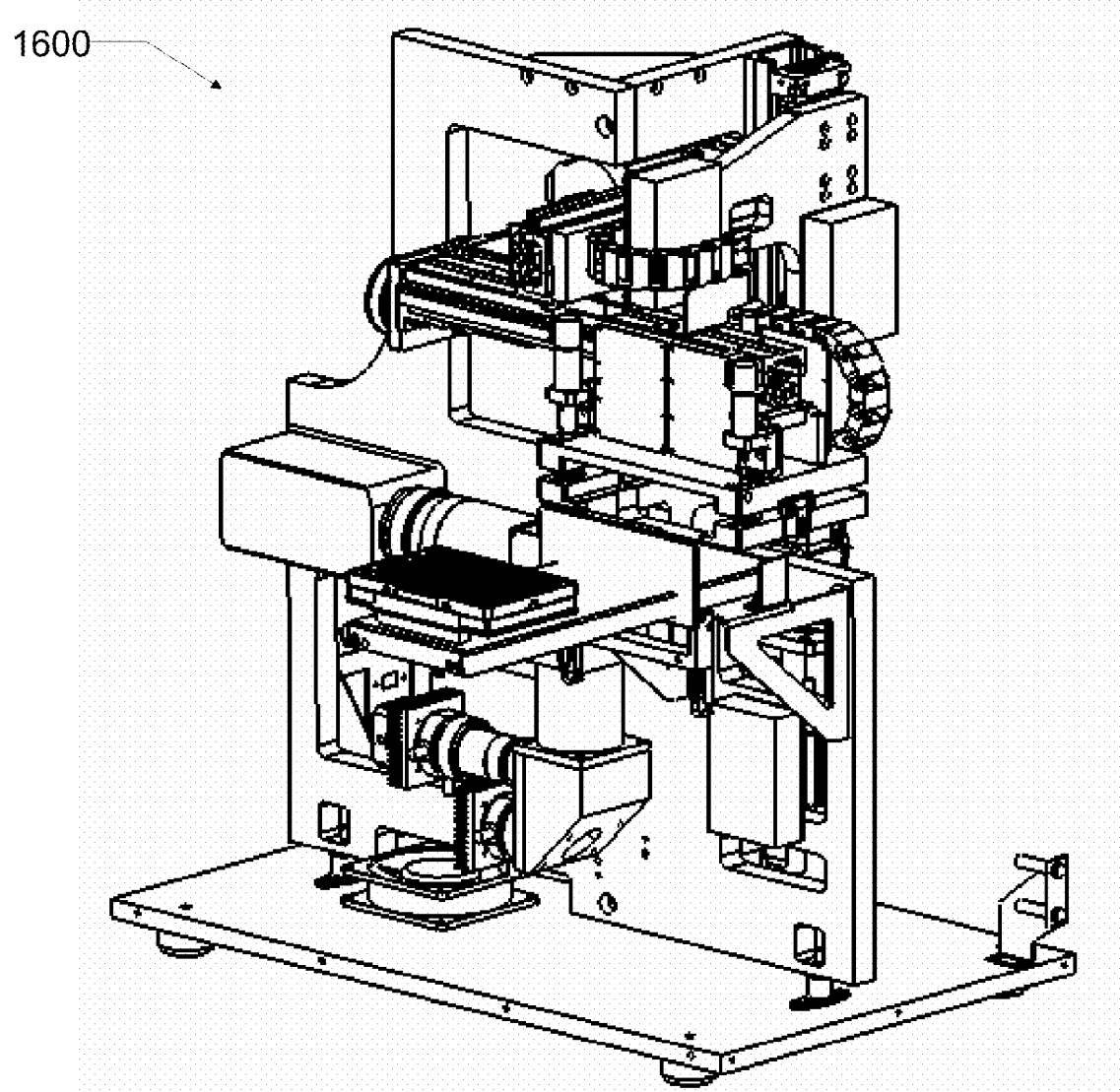
FIG. 17 shows a simplified internal structure of the scanner system that can be used with system for processing biological sensors according to an embodiment of the present invention.

FIG. 17 shows a simplified internal structure of the scanner system 1600 that can be used with system 100 for processing biological sensors according to an embodiment of the present invention. This diagram is merely an example, which should not unduly limit the scope of the claims. One of ordinary skill in the art would recognize many variations, alternatives, and modifications.

Figure 18B:
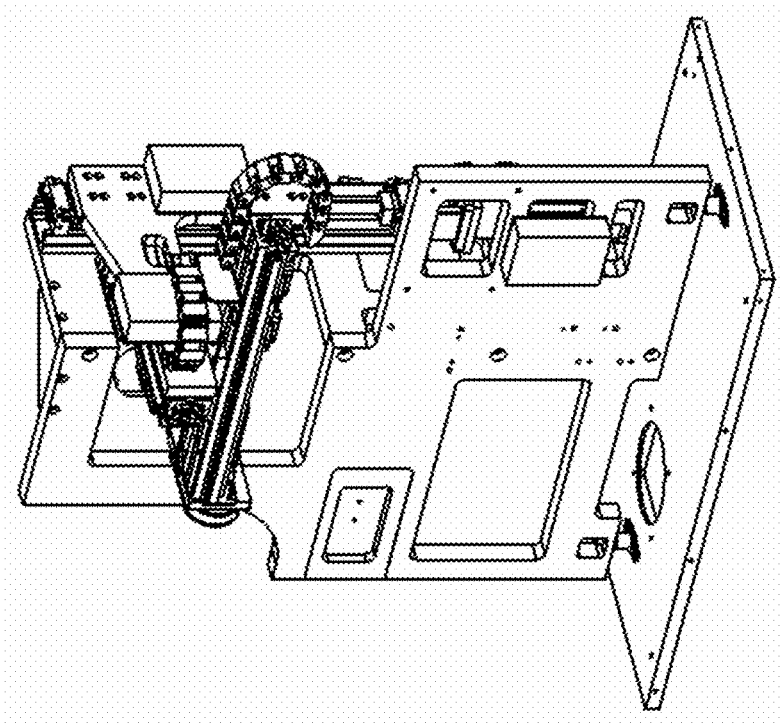
FIGS. 18(A)-(G) show simplified components of the scanner system that can be used with system for processing biological sensors according to an embodiment of the present invention.
Figure 18A:
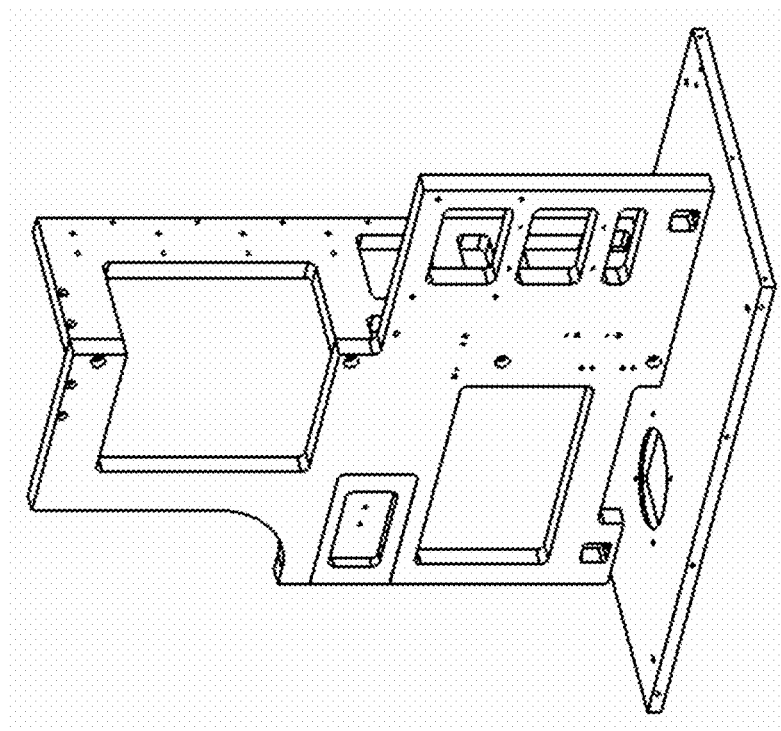
Figure 18D:
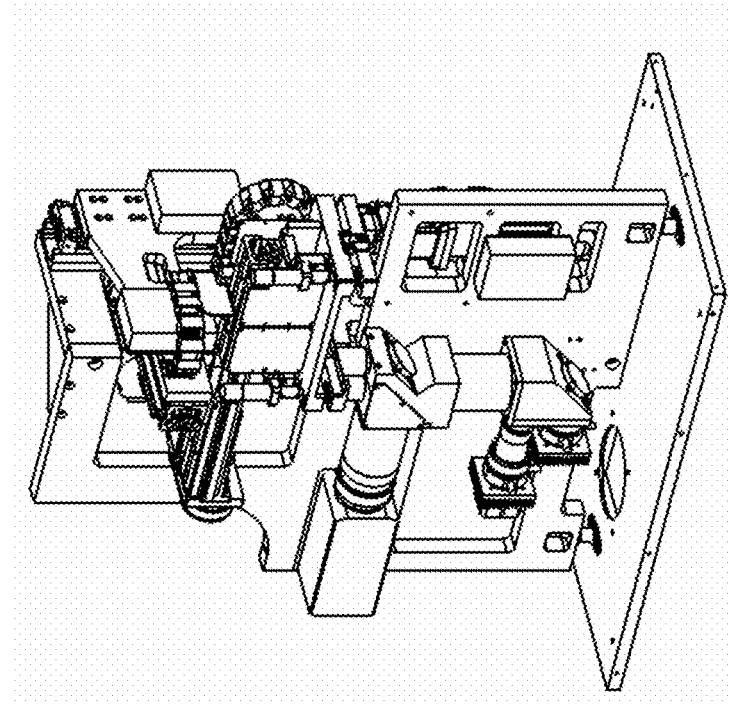
Figure 18C:
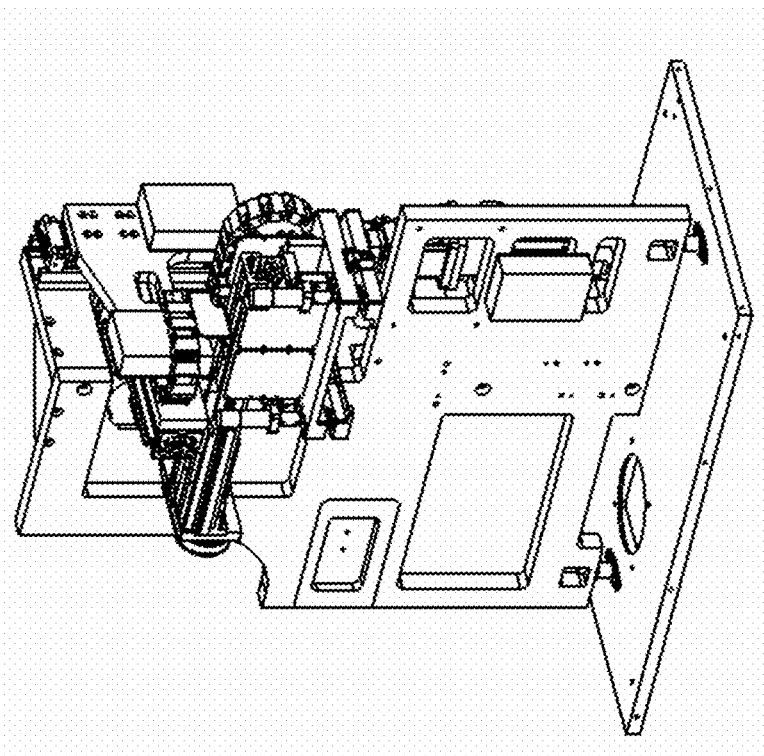
Figure 18F:
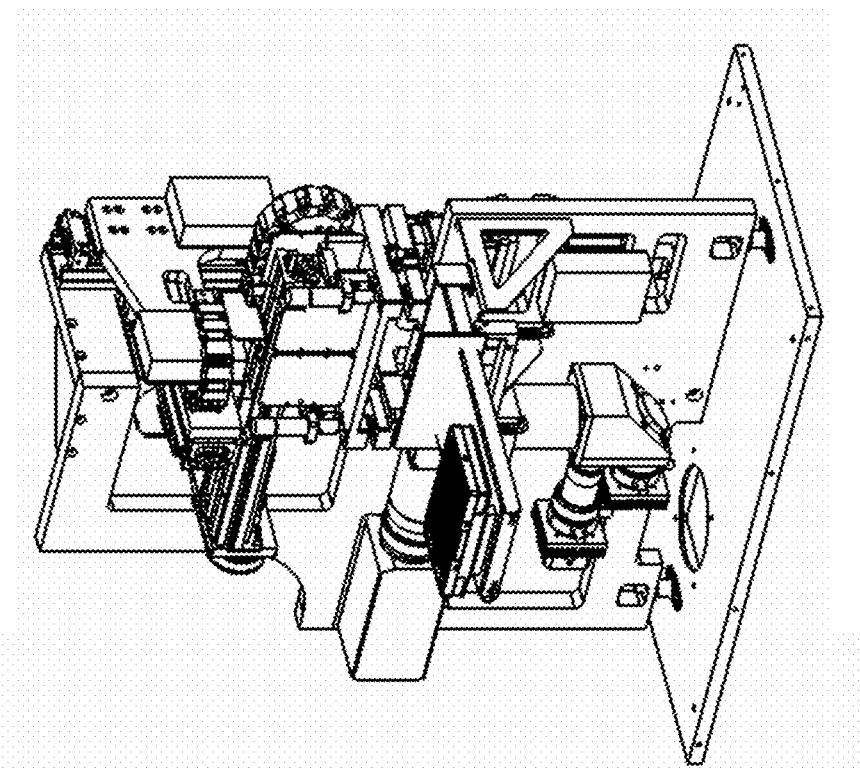
Figure 18E:
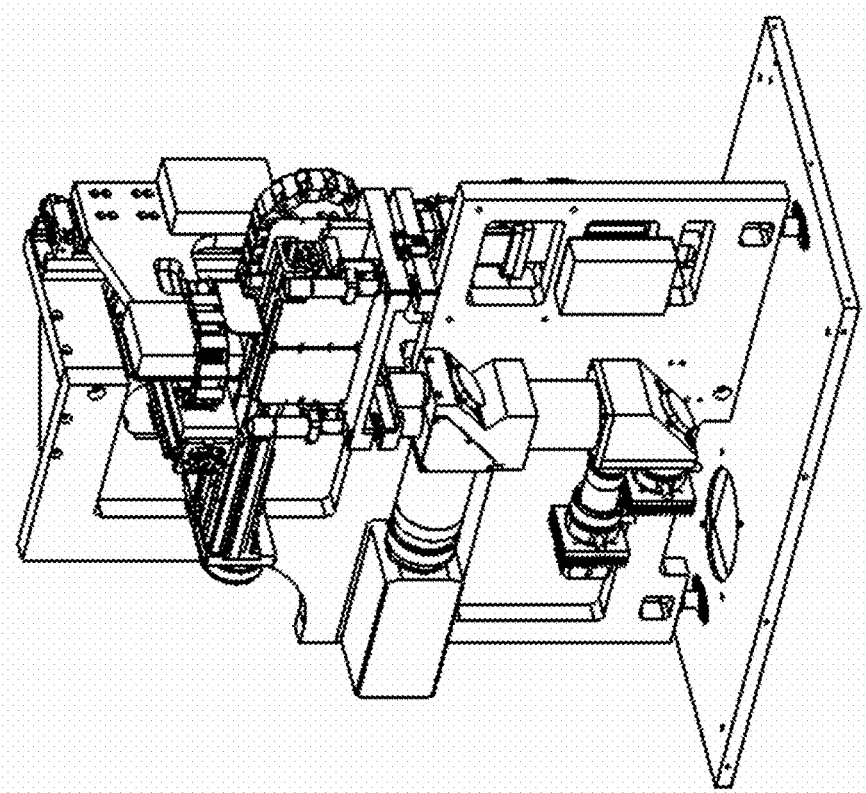
Figure 18G:
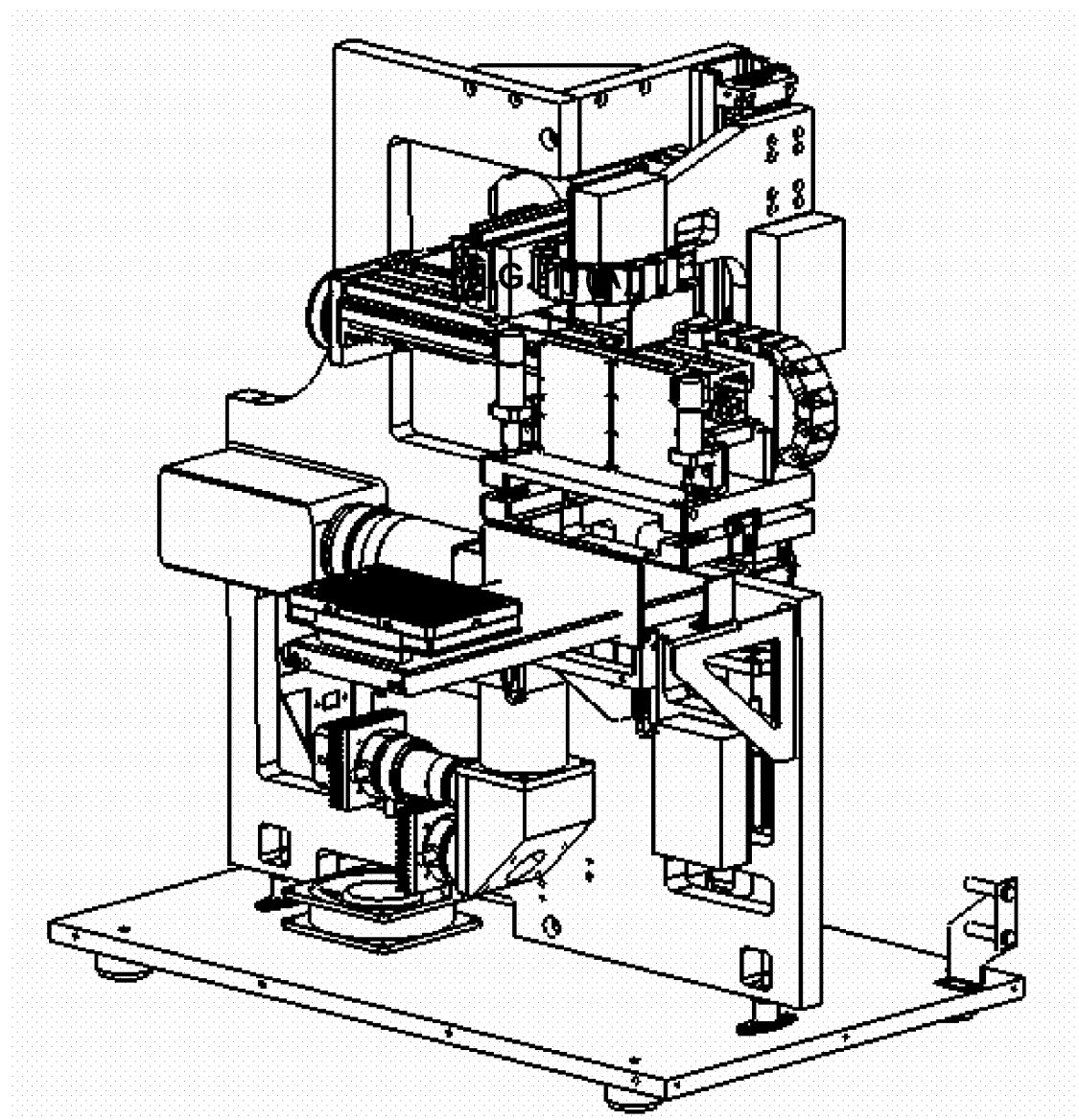

FIGS. 18(A)-(G) show simplified components of the scanner system 1600 that can be used with system 100 for processing biological sensors according to an embodiment of the present invention. These diagram are merely examples, which should not unduly limit the scope of the claims. One of ordinary skill in the art would recognize many variations, alternatives, and modifications. As shown in FIGS. 18(A)-(G), the scanner system 1600 includes an endoskeleton, an XYZ table, a tip/tilt assembly, an optics module, a load tray, a power supply, LEDs, and other components. For example, FIG. 18(A) shows the endoskeleton. In another example, FIG. 18(B) shows the endoskeleton and the XYZ table. In yet another example, FIG. 18(C) shows the endoskeleton, the XYZ table, and the tip/tilt assembly. In yet another example, FIG. 18(D) shows the endoskeleton, the XYZ table, the tip/tilt assembly, and the optics module. In yet another example, FIG. 18(E) shows the endoskeleton, the XYZ table, the tip/tilt assembly, the optics module, and the load tray unextended. In yet another example, FIG. 18(F) shows the endoskeleton, the XYZ table, the tip/tilt assembly, the optics module, and the load tray extended. In yet another example, FIG. 18(G) shows the endoskeleton, the XYZ table, the tip/tilt assembly, the optics module, the load tray extended, the power supply, LEDs, and other components.

Figure 19:
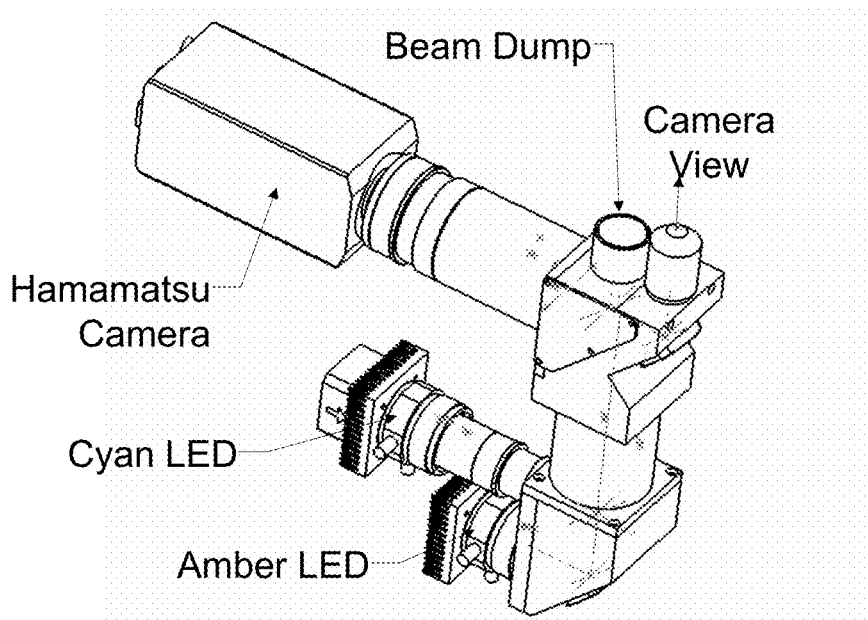
FIG. 19 shows a simplified optics module of the scanner system that can be used with system for processing biological sensors according to an embodiment of the present invention.
Figure 20:
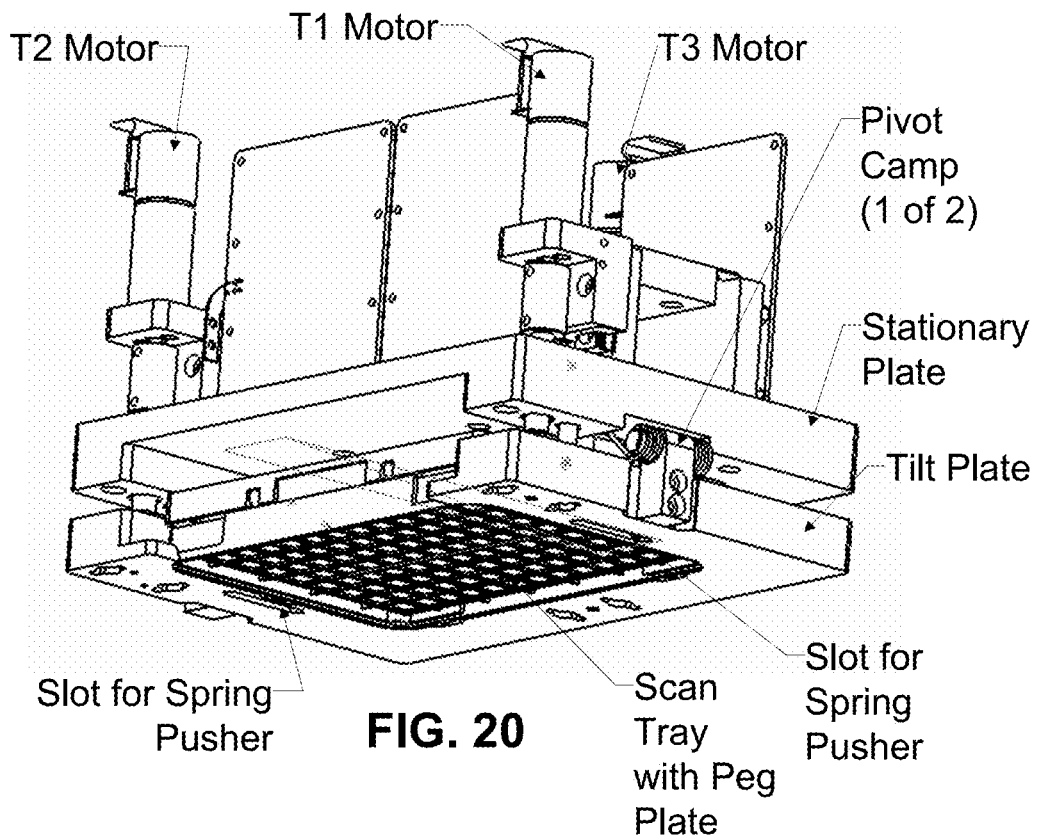
FIG. 20 shows a simplified tip/tilt assembly of the scanner system that can be used with system for processing biological sensors according to an embodiment of the present invention.

FIG. 19 shows a simplified optics module of the scanner system 1600 that can be used with system 100 for processing biological sensors according to an embodiment of the present invention. This diagram is merely an example, which should not unduly limit the scope of the claims. One of ordinary skill in the art would recognize many variations, alternatives, and modifications. For example, the CCD camera is Hamamatsu C8484-05G with CCD array size 1024×1344 (6.45 um pixels) and 12-bit digital output. The output features include read noise 12 e-RMS and dark current 1 e-/pixel/sec. Additionally, the CCD camera has an approximate dynamic range 16000/12 equal to 1300. In another example, the optical design includes the following features:

Nikon 10×, NA=0.40
FOV ~1 mm×1.3 mm, image pixel size=1 um
Excitation LED 530 nm+/−15 nm
Excitation bandpass filter 470-550 nm
3 W excitation LED
Focus illumination LED 590 nm+/−15 nm
Emission bandpass filter 570-610 nm FIG. 20 shows a simplified tip/tilt assembly of the scanner system 1600 that can be used with system 100 for processing biological sensors according to an embodiment of the present invention. This diagram is merely an example, which should not unduly limit the scope of the claims. One of ordinary skill in the art would recognize many variations, alternatives, and modifications.

Figure 21:
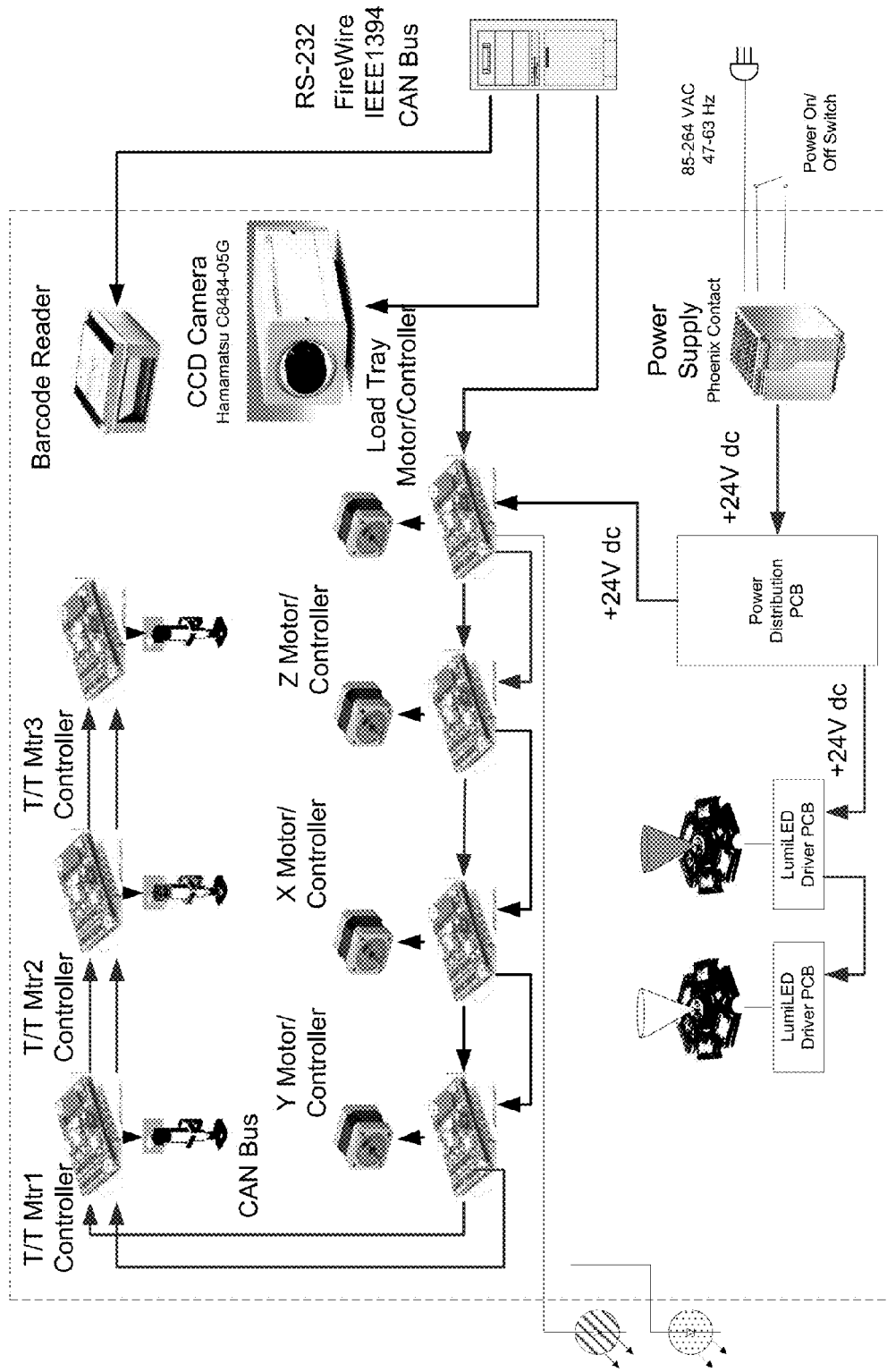
FIG. 21 shows a simplified electrical architecture of the scanner system that can be used with system for processing biological sensors according to an embodiment of the present invention.

FIG. 21 shows a simplified electrical architecture of the scanner system 1600 that can be used with system 100 for processing biological sensors according to an embodiment of the present invention. This diagram is merely an example, which should not unduly limit the scope of the claims. One of ordinary skill in the art would recognize many variations, alternatives, and modifications.

Figure 22A:
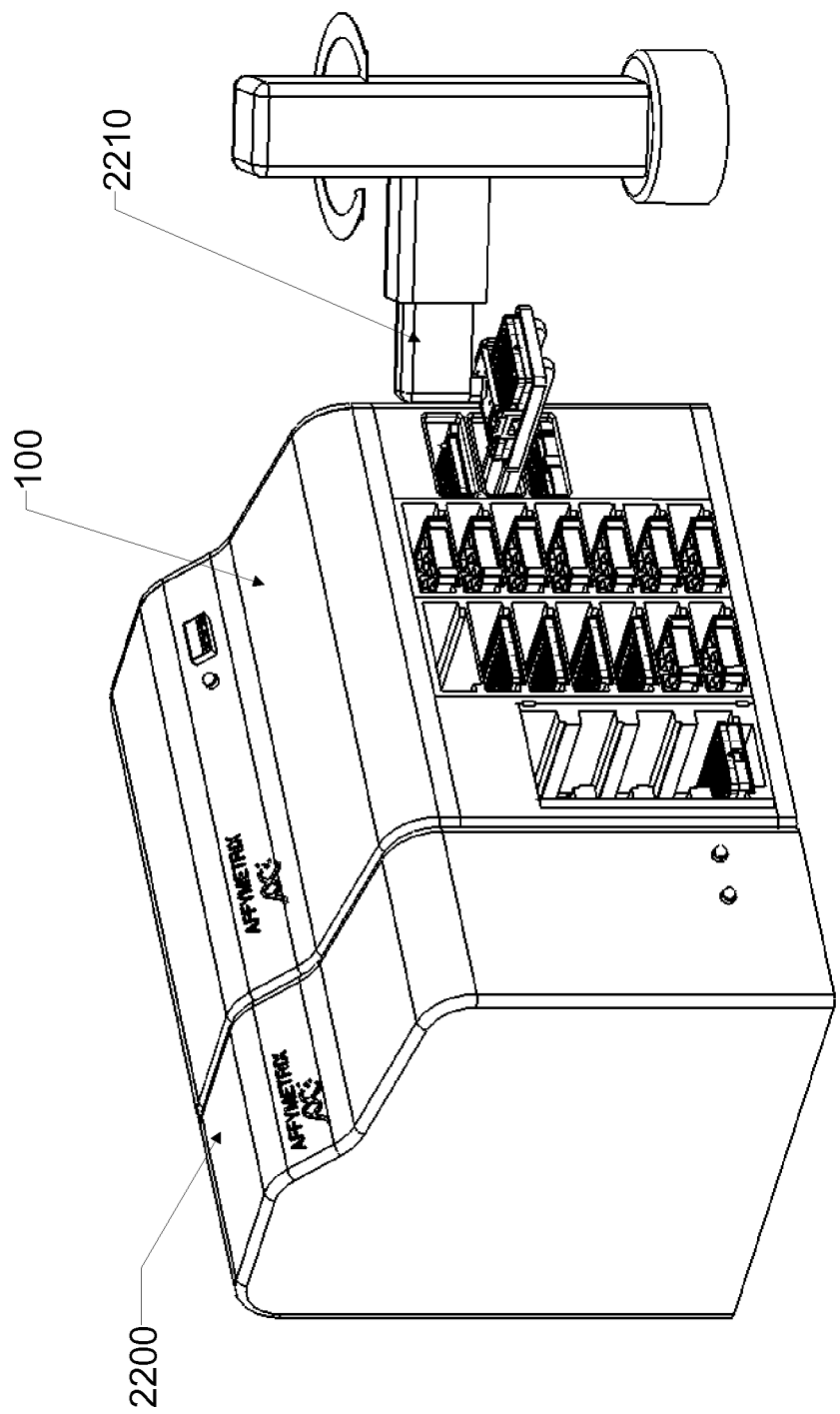
FIGS. 22(A), (B), and (C) show a simplified system with a scanner system for processing biological sensors according to an embodiment of the present invention.
Figure 22B:
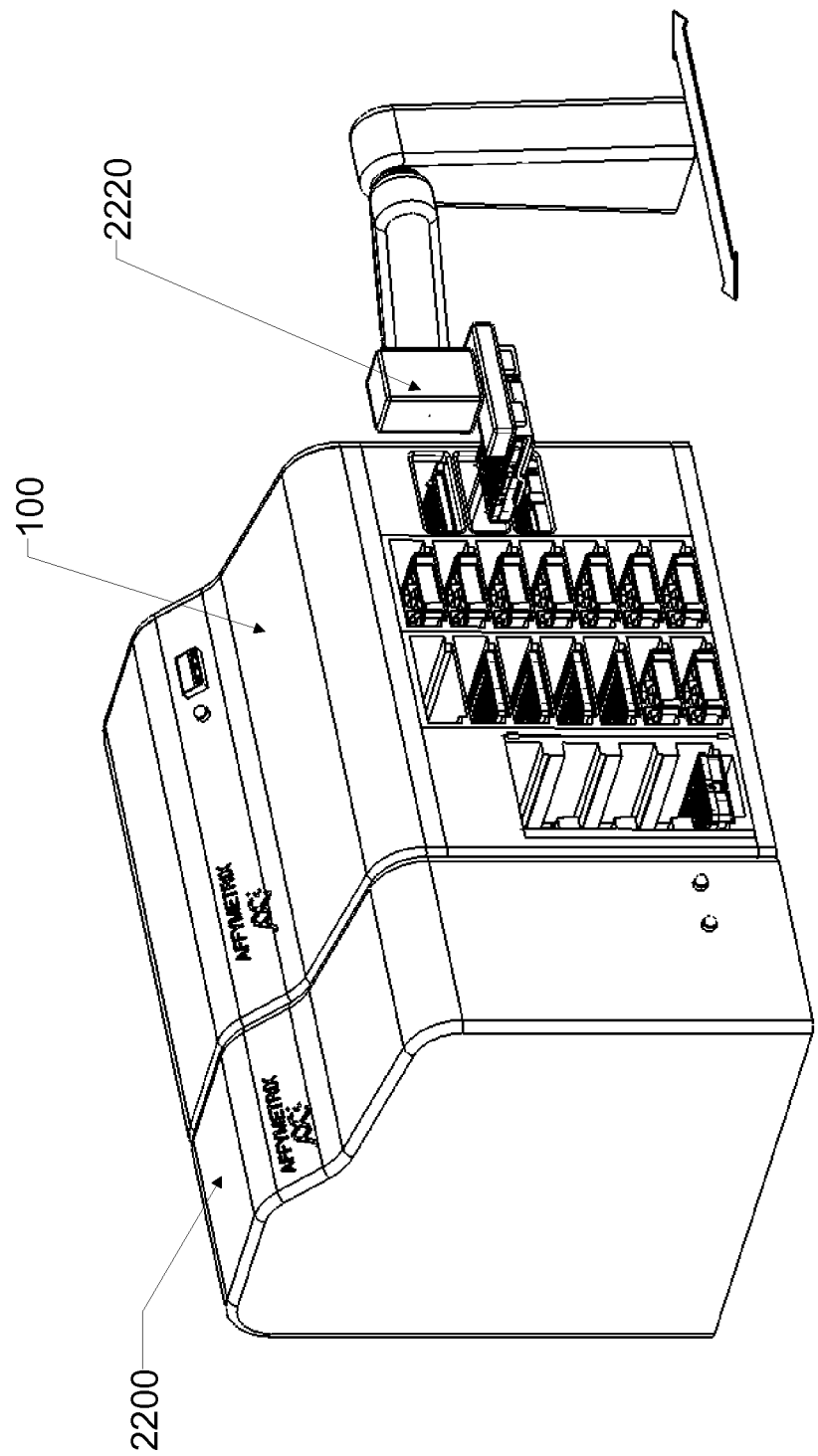
Figure 22C:
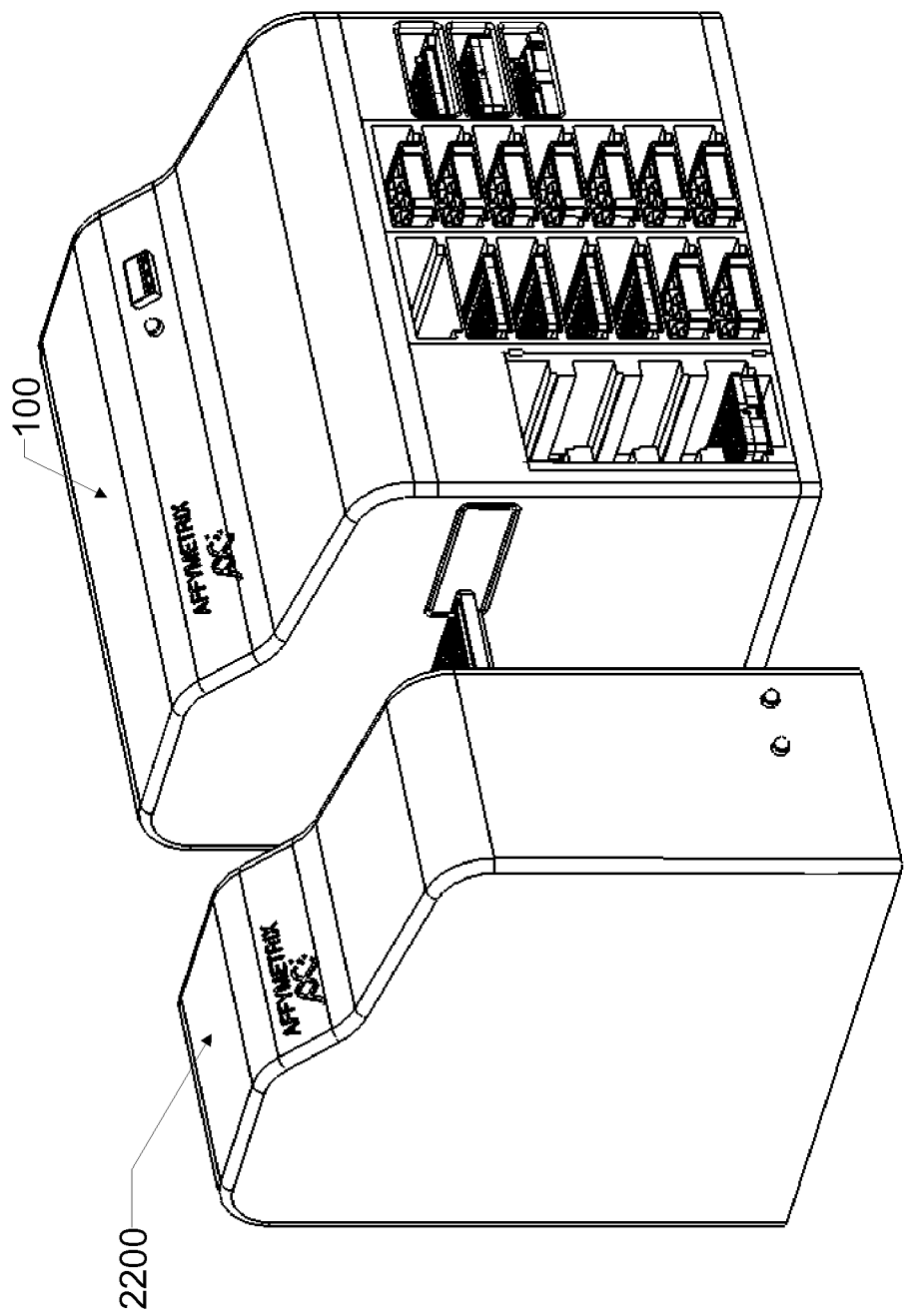

As discussed above and further emphasized here, FIGS. 1-8 and 11-21 are merely examples, which should not unduly limit the scope of the claims. One of ordinary skill in the art would recognize many variations, alternatives, and modifications. For example, FIGS. 22(A), (B), and (C) show a simplified system 100 with a scanner system for processing biological sensors according to an embodiment of the present invention. This diagram is merely an example, which should not unduly limit the scope of the claims. One of ordinary skill in the art would recognize many variations, alternatives, and modifications. The system 100 includes a gripper assembly controlled by a robot arm, such as a twister arm 2210 as shown in FIG. 22(A), or an ORCA arm 2220 as shown in FIG. 22(B). The system 100 can be assembled with the scanner system 2200, such as the scanner system 1600, to form an integrated system. As shown in FIG. 22(C), the system 100 can automatically send and the scanner system 2200 can automatically accept a sensor carrier on a well plate, such as the sensor assembly 900 on the scan tray, if the system 100 and the scanner system 2200 are in contact with each other.

According to another embodiment of the present invention, a system for processing biological sensors includes a support component configured to support a fluidic component. The fluidic component includes at least a first container and a second container. The first container is capable of holding a first volume of a first fluid, and the second container is capable of holding a second volume of a second fluid. Additionally, the system includes a hybridization component configured to perform a hybridization process on a first sensor and a second sensor. Moreover, the system includes a transport component configured to move the first sensor, directly or indirectly, from the hybridization component into the first container and in contact with the first volume of the first fluid. Also, the transport component is further configured to move the second sensor, directly or indirectly, from the hybridization component into the second container and in contact with the second volume of the second fluid. The transport component is further configured to move the first sensor and the second sensor substantially simultaneously. For example, the system is implemented according to the system 100.

According to yet another embodiment of the present invention, a system for processing biological sensors includes a support component configured to support a fluidic component. The fluidic component includes at least a first container and a second container. The first container is capable of holding a first volume of a first fluid, and the second container is capable of holding a second volume of a second fluid. Additionally, the system includes a hybridization component configured to perform a hybridization process on a first sensor and a second sensor based on at least information associated with a predetermined temperature. Moreover, the system includes a transport component including a gripper and at least one motor. The support component includes a drawer for supporting at least the first container and the second container, and the first container and the second container are substantially stationary with respect to the drawer. The gripper is capable of gripping the first sensor and the second sensor substantially simultaneously and of releasing the first sensor and the second sensor substantially simultaneously. The at least one motor is configured to move the gripped first sensor into the first container and in contact with the first volume of the first fluid, move the gripped second sensor into the second container and in contact with the second volume of the second fluid, and move the first sensor and the second sensor substantially simultaneously. For example, the system is implemented according to the system 100.

According to yet another embodiment of the present invention, a method for processing biological sensors includes transferring a first sensor and a second sensor into a system for processing biological sensors. The system includes at least a transport component, a hybridization component, and a fluidic component. The transport component includes a gripper, and the fluidic component includes a first container and a second container. The first container holds a first volume of a first fluid, and the second container holds a second volume of a second fluid. Additionally, the method includes after the transferring a first sensor and a second sensor, performing a hybridization process on at least the first sensor and the second sensor by the hybridization component. Moreover, the method includes after the hybridization process, moving the first sensor from the hybridization component, directly or indirectly, into the first container and in contact with the first volume of the first fluid. Also, the method includes after the hybridization process, moving the second sensor from the hybridization component, directly or indirectly, into the second container and in contact with the second volume of the second fluid. The moving the first sensor and the moving the second sensor are performed by at least the gripper, and the moving the first sensor and the moving the second sensor are performed substantially simultaneously. For example, the system is implemented according to the system 100.

The present invention has various advantages. Certain embodiments of the present invention provide an automated fluidic and hybridization system. For example, the system includes a hybridization oven assembly and provides automatic transportation between the hybridization oven assembly and other components of the system. In another example, the system provides automated transportation to and from a scanner system. Some embodiments of the present invention provide a system that can perform integrated and automated processes for hybridization, wash, and stain. Additionally, coupled with a scanner system, the system can also perform an integrated and automated scanning process. Certain embodiments of the present invention can improve throughput of the hybridization and fluidic system. For example, a plurality of biological sensors, such as microarrays, is processed in parallel. Some embodiments of the present invention can reduce size of the hybridization and fluidic system as well as the scanner system. Certain embodiments of the present invention can reduce cross-contamination between different processes performed on one or more biological sensors. For example, at a given process, different sensors are washed, stained, and/or held in different wells. In another example, a given sensor is washed, stained, and/or held in different wells for different processes respectively. In yet another example, each well is used for at most a single process for at most a single sensor, such as a microarray.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A device for hybridizing, processing, and scanning a plurality of microarrays, the device comprising:
   a fluidic component comprising:
      a plurality of well plates, wherein each well plate comprises a plurality of wells arranged in a plurality of columns and a plurality of rows, wherein each well plate is configured to mate with a peg plate comprising a base, a plurality of pegs arranged in rows and columns on the base, and a plurality of microarrays, each microarray individually attached to one of the plurality of pegs, and wherein each well of the well plate is configured to receive one of the plurality of microarrays when the well plate is mated with a peg plate;
      a first fluidic container; and
      a second fluidic container;
   a support component comprising a plurality of drawer assemblies, wherein each drawer assembly comprises a drawer panel, and wherein each drawer panel is configured to support one or more well plates;
   a hybridization component comprising a hybridization oven, wherein the hybridization oven is configured to hybridize a nucleic acid sample to a microarray, and wherein the hybridization component is fixed to the support component;
   a scanning component fixed to the support component, wherein the scanning component is configured to scan the plurality of microarrays after hybridization and processing;
   a transport component configured to grip, move and release a peg plate, wherein the transport component comprises a gripper assembly having a closed position suitable for gripping a peg plate and an open position suitable for releasing the peg plate, wherein the gripper assembly comprises a base plate, sensors, a motor, a cam, rack and pinion, a spring, two arms, and finger assemblies, wherein the arms extend outward from the base plate substantially parallel to one another with a finger assembly attached to an interior surface of each arm such that the finger assemblies are oppositely facing one another and capable of contacting opposing sides of the support component of a peg plate, wherein the arms are movably joined to one another through the cam, rack and pinion, and the spring, and wherein the motor increases or decreases the distance between the arms by applying force to the cam, thereby moving the gripper between the open and closed positions, and wherein the transport component moves the peg plate within and between the components; and a processing system, wherein the processing system comprises a computer, and wherein the computer is configured to direct the movements of the transport component.

2. The device of claim 1, additionally comprising:
a barcode reader configured to read one or more barcodes on the well plates.

3. The device of claim 1, additionally comprising:
an unclamping station configured to separate a peg plate from a hybridization tray after the plurality of microarrays have been hybridized to nucleic acid samples.

4. The device of claim 3, wherein the hybridization tray comprises a plurality of handles, and wherein the handles are configured to facilitate clamping of the hybridization tray with the peg plate.

5. The device of claim 4, wherein the unclamping station comprises a plurality of fingers, and wherein the fingers are configured to unclamp the peg plate from the hybridization tray.

6. The device of claim 1, wherein the first fluidic container is configured to hold a first washing fluid, and wherein the first fluidic container and the transport component are configured to wash the plurality of microarrays a plurality of times.

7. The device of claim 6, wherein the second fluidic container is configured to hold and heat a second washing fluid, and wherein the second fluidic container and the transport component are configured to wash the plurality of microarrays with the heated second washing fluid.

8. The device of claim 1, wherein each drawer panel is configured to support two well plates in a side-by-side configuration.

9. The device of claim 1, wherein each drawer panel is configured to slide horizontally.

10. The device of claim 1, wherein each drawer panel comprises one or more biasing features configured to align and fix a well plate to the drawer panel.

11. The device of claim 1, wherein each drawer panel (i) is configured to support two well plates in a side-by-side configuration, (ii) is configured to slide horizontally, and (iii) comprises one or more biasing features configured to align and fix two well plates to the drawer panel.

12. The device of claim 11, wherein each drawer assembly additionally comprises a splash guard.

13. The device of claim 1, wherein the plurality of drawer assemblies includes a handoff drawer assembly, wherein the handoff drawer assembly comprises a handoff drawer panel, wherein the transport component is configured to place the peg plate on the handoff drawer panel after hybridization and processing, and wherein the handoff drawer assembly and the transport component are configured to transfer the peg plate from the handoff drawer assembly to the scanning component.

14. The device of claim 1, wherein the scanning component comprises a CCD camera and an XYZ table and a tip-tilt assembly, wherein the XYZ table and tip-tilt assembly are configured to manipulate the peg plate.

15. The device of claim 1, wherein the finger assemblies fit into recesses located on opposing sides of the base of the peg plate.

16. The device of claim 1, wherein the arms of the gripper assembly extend beyond the section used for attaching the finger assemblies.

17. The device of claim 16, wherein the distal end of at least one arm of the gripper assembly comprises a notched flange configured to latch onto a drawer assembly, thereby enabling the transport component to move the drawer assembly between open and closed positions by moving the gripper assembly.

18. The device of claim 1, further comprising a peg plate comprising a base, a plurality of pegs arranged in rows and columns on the base, and a plurality of microarrays, each microarray individually attached to one of the plurality of pegs.

19. The device of claim 18, wherein the peg plate comprises 96 pegs.

20. The device of claim 18, wherein each of the plurality of microarrays has a substantially square shape with a length equal to or less than 10 mm, a width equal to or less than 10 mm, and a thickness equal to or less than 1000 μm.

21. A device for hybridizing, processing, and scanning a plurality of microarrays, the device comprising:
a fluidic component comprising:
a plurality of well plates, wherein each well plate comprises a plurality of wells arranged in a plurality of columns and a plurality of rows, wherein each well plate is configured to mate with a peg plate comprising a base, a plurality of pegs arranged in rows and columns on the base, and a plurality of microarrays, each microarray individually attached to one of the plurality of pegs, and wherein each well of the well plate is configured to receive one of the plurality of microarrays when the well plate is mated with a peg plate;
a first fluidic container configured to wash the plurality of microarrays a plurality of times with a first washing fluid; and
a second fluidic container configured to wash the plurality of microarrays with a second washing fluid, wherein the second fluidic container is additionally configured to heat the second washing fluid;
a barcode reader configured to read one or more barcodes on the well plates;
a support component comprising a plurality of drawer assemblies, wherein each drawer assembly comprises a drawer panel, wherein each drawer panel is configured to support two well plates in a side-by-side configuration and slide horizontally, wherein each drawer panel comprises one or more biasing features configured to align and fix two well plates to the drawer panel, and wherein the drawer assemblies includes a handoff drawer assembly comprising a handoff drawer panel;
a hybridization component comprising a hybridization oven, wherein the hybridization oven is configured to hybridize a nucleic acid sample to a microarray, and wherein the hybridization component is fixed to the support component;

a scanning component fixed to the support component, wherein the scanning component is configured to scan the plurality of microarrays after hybridization and processing;

a transport component configured to grip, move and release a peg plate, wherein the transport component comprises a gripper assembly having a closed position suitable for gripping a peg plate and an open position suitable for releasing the peg plate, wherein the gripper assembly comprises a base plate, sensors, a motor, a cam, rack and pinion, a spring, two arms, and finger assemblies, wherein the arms extend outward from the base plate substantially parallel to one another with a finger assembly attached to an interior surface of each arm such that the finger assemblies are oppositely facing one another and capable of contacting opposing sides of the support component of a peg plate, wherein the arms are movably joined to one another through the cam, rack and pinion, and the spring, and wherein the motor increases or decreases the distance between the arms by applying force to the cam, thereby moving the gripper between the open and closed positions, wherein the transport component moves the peg plate within and between the components, and wherein the transport component and handoff drawer assembly are configured to transfer the peg plate from the handoff drawer assembly to the scanning component;

an unclamping station configured to separate a peg plate from a hybridization tray after the plurality of microarrays have been hybridized to the nucleic acid sample in the hybridization component; and a processing system, wherein the processing system comprises a computer, and wherein the computer is configured to direct the movements of the transport component.

22. The device of claim 21, wherein the finger assemblies fit into recesses located on opposing sides of the base of the peg plate.

23. The device of claim 21, wherein the arms of the gripper assembly extend beyond the section used for attaching the finger assemblies.

24. The device of claim 23, wherein the distal end of at least one arm of the gripper assembly comprises a notched flange configured to latch onto a drawer assembly, thereby enabling the transport component to move the drawer assembly between open and closed positions by moving the gripper assembly.

25. The device of claim 21, further comprising a peg plate comprising a base, a plurality of pegs arranged in rows and columns on the base, and a plurality of microarrays, each microarray individually attached to one of the plurality of pegs.

26. The device of claim 25, wherein the peg plate comprises 96 pegs.

27. The device of claim 25, wherein each of the plurality of microarrays has a substantially square shape with a length equal to or less than 10 mm, a width equal to or less than 10 mm, and a thickness equal to or less than 1000 µm.

* * * * *